(12) United States Patent
Kawase et al.

(10) Patent No.: US 7,481,913 B2
(45) Date of Patent: Jan. 27, 2009

(54) HIGH-RESOLUTION GAS CONCENTRATION MEASURING APPARATUS

(75) Inventors: Tomoo Kawase, Aichi-ken (JP); Eiichi Kurokawa, Okazaki (JP)

(73) Assignee: DENSO Corporation, Kariya (JP)

( * ) Notice: Subject to any disclaimer, the term of this patent is extended or adjusted under 35 U.S.C. 154(b) by 724 days.

(21) Appl. No.: 10/703,510

(22) Filed: Nov. 10, 2003

(65) Prior Publication Data

US 2004/0089545 A1    May 13, 2004

(30) Foreign Application Priority Data

Nov. 8, 2002  (JP) ............................. 2002-325659
Jun. 30, 2003  (JP) ............................. 2003-187371

(51) Int. Cl.
*G01N 27/41*    (2006.01)

(52) U.S. Cl. ...................... 204/406; 204/425; 73/23.32

(58) Field of Classification Search ................. 204/406, 204/424, 426, 427; 205/781, 784.5; 73/23.31, 73/23.32

See application file for complete search history.

(56) References Cited

U.S. PATENT DOCUMENTS

| 5,810,997 A | 9/1998 | Okazaki et al. |
| 5,980,710 A | 11/1999 | Kurokawa et al. |
| 6,383,354 B1 | 5/2002 | Kurokawa et al. |
| 6,478,940 B1 | 11/2002 | Suzuki et al. |

FOREIGN PATENT DOCUMENTS

| EP | 0 318 972 | 6/1989 |
| JP | 1143961 | 6/1989 |
| JP | 9061397 | 3/1997 |
| JP | 11-37971 | 2/1999 |
| JP | 2000155109 | 6/2000 |

OTHER PUBLICATIONS

JPO Official communication issued on Jul. 8, 2008 in corresponding Japanese Application No. 2003-187371 w/ an at least partial English language translation thereof.

*Primary Examiner*—Kaj K Olsen
(74) *Attorney, Agent, or Firm*—Nixon & Vanderhye P.C.

(57) ABSTRACT

A gas concentration measuring apparatus for use in air-fuel ratio control of motor vehicle engines is provided which includes a laminated sensor element and a sensor circuit. The sensor circuit includes a current-measuring resistor, at least one amplifier, and A/D converters. The current-measuring resistor functions to measure a current signal flowing through the sensor element produced upon application of the voltage to the sensor element. The amplifier works to amplify the current signal to output it to one of the A/D converters to determine the concentration of the air-fuel ratio within one of a plurality of measurement ranges defined within the wide gas concentration measuring range. The amplification of the current signal results in expansion of the level of the input to the A/D converter, thus enhancing the resolution in determining the air-fuel ratio.

14 Claims, 17 Drawing Sheets

HIGH-RESOLUTION GAS CONCENTRATION MEASURING APPARATUS

BACKGROUND OF THE INVENTION

1. Technical Field of the Invention

The present invention relates generally to a gas concentration measuring apparatus which may be used in measuring the concentration of a preselected component of exhaust emissions of automotive engines, and more particularly to such a gas concentration measuring apparatus designed to ensure high resolution in measuring the concentration of gas over a desired range.

2. Background Art

As a typical one of the above type of gas concentration measuring apparatuses, an automotive air-fuel ratio measuring apparatus is known which works to measure the concentration of oxygen ($O_2$) contained in exhaust emissions of motor vehicle engines as indicating an air-fuel ratio of a mixture. The result obtained is used in an air-fuel ratio control system consisting of an engine ECU etc. Stoichiometric burning controls to bring the air-fuel ratio near the stoichiometric air-fuel ratio under feedback control and lean-burn controls to bring the air-fuel ratio to within a given lean range under feedback control are being developed. In recent years, emission regulations or on-board diagnostic (OBD) requirements have been increasingly tightened. Improvement of the stoichiometric burning controls is, thus, being sought. Additionally, there is an increasing need for expanding an air-fuel ratio measurable range up to an atmospheric range as well as the lean range that is a typical air-fuel ratio controlling range. For instance, a sensor malfunction monitoring system is known to meet the OBD requirements which works to monitor a deterioration of a gas sensor such as clogging resulting in a decrease in sensor output current during a fuel cut-off (i.e., when exhaust gasses are equivalent to air) under a given operating engine condition. It is also essential to improve fuel efficiency as well as exhaust emissions. It is further essential to feedback-control a rich mixture at high load engine operating conditions.

Typically, lean-burn engines having a NOx occluding/reducing catalyst installed in an exhaust system encounter the problem in that a large amount of NOx is occluded in the catalyst during a lean-burn engine operation, which results in lowered ability of absorbing NOx emissions. Additionally, typical fuel contains sulfur, thus poisoning the NOx occluding/reducing catalyst. In order avoid these problems, the rich air-fuel ratio controls have been implemented to recovery the NOx absorbing ability or revive the sulfur-poisoned catalyst. For these reasons, the air-fuel ratio control system is required to expand the air-fuel ratio measurable range and enhance the accuracy of measuring the air-fuel ratio within such a range.

In general, oxygen sensors are known as air-fuel (A/F) sensors to determine an exhaust gas air-fuel ratio. Such sensors are of two types: one is a cup-shaped A/F sensor and the other is a laminated A/F sensor (also called a multilayered A/F sensor). The cup-shaped A/F sensor is equipped with a sensor element made up of a cup-shaped solid electrolyte body, a pair of electrodes affixed to outer and inner surfaces of the solid electrolyte body, and a diffusion layer surrounding the solid electrolyte body. The solid electrolyte body also has installed in an inner chamber thereof a bar heater which serves to heat the whole of the sensor element to kept in a desired activate condition. The inner chamber of the solid electrolyte body forms an air duct leasing to the atmosphere.

The laminated A/F sensor is equipped with a sensor element made of a strip-shaped lamination of a solid electrolyte body, a diffusion layer, and an insulating layer which defines an air duct. The solid electrolyte body has affixed thereto a pair of electrodes which are opposed to each other. The insulating layer has a heater embedded therein.

Comparing between the cup-shaped A/F sensor and the laminated A/F sensor structurally, we found the following problems and advantages. The volume or mass of a portion of the sensor element of the cup-shaped A/F sensor heated for activation is greater than that of the laminated A/F sensor, thus resulting in an increased time required to complete the activation at cold engine start-up, a difficulty in activating the sensor element early, and an increased electric power consumed by the heater. In contrast, the laminated A/F sensor has the advantages that it is easy to install the heater integrally in the sensor element and to decrease the volume of the sensor element to accelerate the activation thereof, which results in a decrease in electric power consumed by the heater. For these reasons, the laminated A/F sensors have become prevalent.

If the size of the sensor element of the laminated A/F sensors is decreased, the volume of the air duct needs to be decreased. The decrease in volume of the air duct requires decreasing an electric current flowing through the sensor element (will also be referred to as a sensor element current below). Specifically, when exhaust gasses of the engine are rich, the sensor is so controlled that oxygen ($O_2$) contained in air within the air duct is pumped into a gas chamber of the sensor element filled with the exhaust gasses. If the sensor element current is great, it causes a pumped amount of the oxygen to increased, which requires the need for increasing the size of the air duct. It is, thus, necessary for decreasing the size of the sensor element to decrease the sensor element current. This may be achieved by decreasing the size of the electrodes or increasing a diffusion rate of the diffusion layer (e.g., decreasing the porosity of the diffusion layer).

FIG. 16 illustrates an example of conventional electric circuits designed to measure the sensor element current flowing through the laminated A/F sensor.

A reference voltage source 153 is connected to a positive (+) terminal of a sensor element 150 through an operational amplifier 151 and a current-measuring resistor 152. A voltage applying control circuit 155 is connected to a negative (−) terminal of the sensor element 150 through an operational amplifier 154. The voltage appearing at a terminal A leading to an end of the resistor 152 is kept identical with the reference voltage Vf. The sensor element current flows through the current-measuring resistor 152 to change the voltage appearing at a terminal B. For instance, when the exhaust gasses are on the lean side, the current flows from the positive terminal to the negative terminal of the sensor element 150, so that the voltage appearing at the terminal B rises. Alternatively, when the exhaust gasses are on the rich side, the current flows from the negative terminal to the positive terminal of the sensor element 150, so that the voltage appearing at the terminal B drops. The voltage application control circuit 155 works to monitor the voltage at the terminal B and determine the voltage to be applied to the sensor element 150 (i.e., the voltage at a terminal D) as a function of the monitored voltage. The voltage at the terminal B is outputted as indicating the air-fuel ratio to a microcomputer (not shown) through an operational amplifier 156.

Keeping the sensor element 150 in a desired activate condition requires bringing an ac impedance Zac of the sensor element 150 into agreement with a given target value. Energization of a heater installed in the sensor element 150 is, thus, controlled as a function of a deviation of the impedance Zac from the target value. The determination of the impedance Zac is achieved by sweeping the voltage developed at the terminal D in an ac form through the voltage application control circuit 155, measuring a change in voltage ΔV at the terminal D, calculating a current change ΔI derived by dividing a change in voltage at the terminal B by a resistance value of the resistor 152, and dividing the voltage change ΔV by the current change ΔI(i.e., Zac=ΔV/ΔI).

Differences in sensor characteristic and solution in determining the air-fuel ratio between the above described cup-shaped A/F sensor and the laminated A/F sensor will be discussed below. It is assumed that an air-fuel ratio measurable range of the A/F sensors is between an air-fuel ratio of 11 to an air-fuel ratio in the atmospheric air (which will also be referred to as a free-air ratio below).

It is assumed that the cup-shaped A/F sensor is designed to meet electrical specifications as shown below.

When the exhaust gasses show the free-air ratio, the sensor element produces a current of 2.5 mA. When the A/F ratio is 11, the sensor element produces a current of −13 mA. The impedance Zac is 22Ω. The dc internal resistance Ri is 30Ω. The sensor control circuit, as illustrated in FIG. 16, has the following electrical specifications. A change in voltage used to measure the impedance Zac is ±0.3V. A current-measuring resistance is 63Ω. The reference voltage Vƒ is 2.5V.

When the exhaust gasses have a stoichiometric air-fuel ratio, the voltage appearing at the terminal B will be identical with that at the terminal A. An sensor output of the operational amplifier 156, i.e., the voltage at the terminal B has values, as indicated below, at the free-air ratio and an air-fuel ratio of 11, respectively.

Output (free-air ratio)=2.5V+63Ω×25 mA=4.075V

Output(*A/F*=11)=2.5V+63Ω×(−13 mA)=1.681V

If the sensor output is inputted to a microcomputer through a 10-bit A/D converter to determine the A/F ratio, the measurement resolution within a range of an air-fuel ratio of 11 to the free-air ratio is (4.075−1.681)/5V×1024=490

If a change in the sensor element current per air-fuel ratio of one near the stoichiometric air-fuel ratio is 2 mA, the measurement resolution is 2 mA×63Ω/5V×1024=490

The determination of the impedance Zac is achieved by sweeping the voltage at the terminal D to negative and positive sides. The voltage appearing at the terminal B undergoes changes, as shown below, at the free-air ratio and an air-fuel ratio of 11 due to the change in voltage at the terminal D to the positive side.

Voltage at *B*=4.075V+63Ω×(0.3V/22Ω)=4.934V

Voltage at *B*=1/681V+63Ω×(0.3V/22Ω)=2.54V

The change in voltage at the terminal D to the negative side results in a change in voltage at the terminal B. When the air-fuel ratio is 11, the voltage at the terminal B has a minimum value as shown below.

Voltage at *B*=1.681V+63Ω×(−0.3V/22Ω)=0.822V

It is found that when the voltage at the terminal D is changed to the positive and negative sides to determine the impedance Zac, a resultant value of the voltage at the terminal B lies within an operational voltage range (0 to 5V) of the A/D converter of the microcomputer. Specifically, the sensor control circuit, as shown in FIG. 16, is so designed that the impedance Zac can be determined correctly.

The laminated A/F sensor is, as described above, so designed to decrease the sensor element current. For instance, the sensor element current produced in the laminated A/F sensor is approximately one-tenth of that in the cup-shaped A/F sensor.

It is assumed that the laminated A/F sensor is so designed to meet electrical specifications as shown below.

When the exhaust gasses show the free-air ratio, the sensor element produces a current of 2.5 mA. When the A/F ratio is 11, the sensor element produces a current of −1.3 mA. The impedance Zac is 28Ω. The dc internal resistance Ri is 60Ω. The sensor control circuit, as illustrated in FIG. 16, has the following electrical specifications. A change in voltage used to measure the impedance Zac is ±0.3V. A current-measuring resistance is 185Ω. The reference voltage Vƒ is 2.5V.

When the exhaust gasses have a stoichiometric air-fuel ratio, the voltage appearing at the terminal B will be identical with 2.5V at the terminal A. An sensor output of the operational amplifier 156, i.e., the voltage at the terminal B has values, as indicated below, at the free-air ratio and an air-fuel ratio of 11, respectively.

Output (free-air ratio)=2.5V+185Ω×2.5 mA=2.9625V

Output (*A/F*=11)=2.5V+185Ω×(−1.3 mA)=2.2595V

It will be apparent from the above that the laminated A/F sensor is so designed that the voltages at terminals B and D can be measured correctly to determine the impedance Zac. If the voltage at the terminal D is changed by 0.3V to the positive side to determine the impedance Zac, the voltage developed at the terminal B has values, as indicated below, at the free-air ratio and an air-fuel ratio of 11, respectively.

Voltage at B=4.9446V

Voltage at B=4.2416V

If the voltage at the terminal D is changed by 0.3V to the positive side to determine the impedance Zac, the voltage developed at the terminal B has a minimum value, as shown below, at an air-fuel ratio of 11.

Voltage at B=0.277V

If the sensor output is inputted to a microcomputer through a 10-bit A/D converter to determine the A/F ratio, the measurement resolution within a range of an air-fuel ratio of 11 to the free-air ratio is (2.9625−2.2595)/5V×1024=144

It is found that the measurement resolution of the laminated A/F sensor is approximately 0.3 times that of the cup-shaped A/F sensor (i.e., 144/490=0.294).

If a change in the sensor element current per air-fuel ratio of one near the stoichiometric air-fuel ratio is 0.2 mA, the measurement resolution is 0.2 mA×185Ω/5V×1024=7

It is found that the measurement resolution of the laminated A/F sensor is approximately 0.3 times that of the cup-shaped A/F sensor (i.e., 7/25=0.28).

The reasons why the measurement resolution of the laminated A/F sensor is lower than that of the cup-shaped A/F sensor will be discussed below.

The sensor element current produced in the laminated A/F sensor is, as described above, decreased to approximately one-tenth of that of the cup-shaped A/F sensor. Thus, if the air-fuel ratio measurable range is between an air-fuel ratio of 11 and the free-air ratio, a range of the sensor element current in the cup-shaped A/F sensor is between −13 mA and 25 mA (=38 mA). A range of the sensor element current in the laminated A/F sensor is between −1.3 mA and 2.5 mA (=3.8 mA). An ac current produced when the impedance Zac is measured in the cup-shaped A/F sensor is 13.6 mA (=0.3V/22Ω). An ac current produced when the impedance Zac is measured in the laminated A/F sensor is 10.7 mA (=0.3V/28Ω). The current produced to measure the impedance Zac in the cup-shaped A/F sensor is 35.8% (13.6 mA/38 mA=0.358) of the sensor element current produced to measure the air-fuel ratio. The current produced to measure the impedance Zac in the laminated A/F sensor is 281.6% (10.7 mA/3.8 mA=2.816) of the sensor element current produced to measure the air-fuel ratio.

It is found that a ratio of the current to measure the impedance Zac to the sensor element current to measure the air-fuel ratio in the laminated A/F sensor is much greater than that in the cup-shaped A/F sensor. The resistance value of a resistor (i.e., the resistor 152 in FIG. 16) used to measure the sensor element current in the laminated A/F sensor must, therefore, be set smaller than that in the cup-shaped A/F sensor, which results in decreased resolution in determining the air-fuel ratio.

If the dc internal resistance value (or ac impedance Zac) of the sensor element of the laminated A/F sensor is increased, it will result in a decrease in current to measure the impedance Zac, so that a ratio of the current to measure the impedance Zac to the sensor element current to measure the air-fuel ratio is decreased. The increase in dc internal resistance of the sensor element, however, results in a change in sensor characteristic (see FIG. 3), which leads to a difficulty in controlling the voltage applied to the sensor element to measure the air-fuel ratio accurately. It is, thus, advisable that the dc internal resistance of the sensor element be not changed.

Japanese Patent First Publication No. 11-37971 teaches techniques for improving resolution in measuring the air-fuel ratio within a wide range. FIG. 17 illustrates a sensor control circuit installed in a gas concentration measuring apparatus as disclosed in the publication. The same reference numbers as employed in FIG. 16 refer to the same parts, and explanation thereof will be omitted here.

Two resistors 161 and 162 are connected in series to measure the current produced in the sensor element 150 (i.e., the sensor element current). A switch 163 is installed which establishes one of connections of the operational amplifier 156 to the terminals B and C selectively as a function of an instantaneous value of the air-fuel ratio. Specifically, when exhaust gasses have at the free-air ratio, the switch 163 closes between the operational amplifier 156 and the terminal C. The sensor element current is measured through the resistor 161 and outputted through the operational amplifier 156. When the exhaust gasses have the stoichiometric air-fuel ratio, the switch 163 closes between the operational amplifier 156 and the terminal B. The sensor element current is measured through the resistors 161 and 162 and outputted through the operational amplifier 156. This ensures the accuracy of measuring the air-fuel ratio over the wide range and improves it especially within a range in the vicinity of the stoichiometric air-fuel ratio.

The structure of FIG. 17, however, has the drawback in that in a case where the laminated A/F sensor is employed, a ratio of the current to measure the impedance Zac to the sensor element current to measure the air-fuel ratio is much greater than that in the cup-shaped A/F sensor, thus resulting in decreased resolution in determining the air-fuel ratio. The problem of the measurement resolution decreasing with a decrease in sensor element current is still standing unsolved.

SUMMARY OF THE INVENTION

It is therefore a principal object of the invention to avoid the disadvantages of the prior art.

It is another object of the invention to provide a gas concentration measuring apparatus designed to ensure high accuracy or resolution of measured concentration of gas over a desired wide range.

According to one aspect of the invention, there is provided a gas concentration measuring apparatus which may be employed in determining an air-fuel ratio of an automotive engine for use in air-fuel ratio control. The gas concentration measuring apparatus comprises: (a) a gas concentration sensor equipped with a sensor element made of a solid electrolyte material working to produce an electric signal as a function of a concentration of a preselected component of gasses over a given wide gas concentration measuring range; and (b) a sensor circuit including a current-measuring resistor, a plurality of amplifiers, and A/D converters, the sensor circuit working to apply a voltage to the sensor element. The current-measuring resistor functions to measure a current signal flowing through the sensor element produced upon application of the voltage to the sensor element. The amplifiers have predetermined amplification factors different from each other and work to amplify the current signal as measured by the current-measuring resistor to output the amplified current signal to the A/D converters to determine the concentration of the preselected component of the gasses within a plurality of measurement ranges defined within the given wide gas concentration measuring range, respectively.

The amplification of the current signal results in expansion of the level of the signals inputted to the A/D converters either to a positive or a negative side, thereby enhancing resolution in determining the concentration of the component of the gasses. The use of the amplifiers one in each of the measurement ranges defined over the wide gas concentration measuring range permits the amplifiers to operate independently in a desired manner, thereby enabling the resolution to be enhanced in each of the measurement ranges.

In the preferred mode of the invention, the plurality of measurement ranges include a first measurement range and a second measurement range narrower than the first measurement range. The plurality of amplifiers include a first amplifier which has an amplification factor m and serves to produce a wide range output used to determine the concentration of the preselected component within the first measurement range and a second amplifier which has an amplification factor n and serves to produce a narrow range output used to determine the concentration of the preselected component within the second measurement range. The amplification factor m is smaller than the amplification factor n, thereby enhancing the resolution greatly within the second measurement range.

The plurality of measurement ranges may include an overall measurable range occupying the whole of the given wide gas concentration measuring range and a partial measurable range occupying a portion of the overall measurable range. The first amplifier serves to produce the wide range output used to determine the concentration of the preselected component within the overall measurable range. The second amplifier serves to produce the narrow range output used to determine the concentration of the preselected component within the partial measurable range The gas concentration measuring apparatus may further comprise a resistance measuring circuit working to change one of a voltage and a current applied to the sensor element in an ac form and measure one of a resultant change in voltage and a resultant change in current through the current-measuring resistor to determine a resistance of the sensor element.

The sensor element may be so designed that the change in current to determine the resistance of the sensor element is greater than the current signal.

The sensor element may be formed by a lamination of a solid electrolyte plate, a diffusion layer, and an insulating layer which has an oxygen reference chamber defined therein.

The sensor element may be so designed as to measure an air-fuel ratio of a burned gas over the given wide gas concentration measuring range.

The sensor element may be so designed as to measure an air-fuel ratio of a burned gas over the given wide gas concentration measuring range. The partial measurable range may include a stoichiometric air-fuel ratio.

The sensor element may alternatively be formed by a lamination of a pump cell working to pump oxygen into or out of a gas chamber defined in the sensor element filled with the gasses and an oxygen sensor cell working to output a signal as a function of concentration of oxygen contained in the gasses. The sensor circuit controls the pump cell so as to keep the signal outputted by the oxygen sensor cell at a given value.

The sensor circuit works to produce a voltage as a function of an internal resistance of the sensor element.

The gas concentration sensor may be implemented by an air-fuel ratio sensor designed to measure an air-fuel ratio of a burned gas over the given wide gas concentration measuring range.

The sensor element may alternatively include a plurality of cells made of a solid electrolyte material, one of which forms a first cell working to pump oxygen into or out of a gas chamber defined in the sensor element filled with the gasses, and another of which forms a second cell working to output a signal as a function of concentration of the preselected component of the gasses into or form which the oxygen is pumped by the first cell.

Each of the amplifiers is connected to the current-measuring resistor so that voltage developed across ends of the current-measuring resistor is applied across a positive and a negative terminal of the operational amplifier. The sensor circuit includes a feedback current path for each of the amplifiers and an operational amplifier installed in each of the feedback current paths to absorb a feedback current of a corresponding one of the amplifiers.

The current-measuring resistor has a first and a second terminal. The sensor circuit works to apply a fixed reference voltage to the first terminal of the current-measuring resistor, change one of a voltage and a current applied to the sensor element in an ac form, and measure a resultant voltage developed at the second terminal to determine a resistance of the sensor element. The sensor circuit has a switch working to open and close between the second terminal and the amplifiers. The switch opens between the second terminal and the amplifiers to eliminate undesirable changes in outputs of the amplifiers during determination of the resistance of the sensor element.

The sensor circuit may have a capacitor installed between the switch and the amplifiers to hold a voltage developed immediately before the switch is opened.

The sensor circuit may have clamping circuits disposed in output lines leading to output terminals of the amplifiers, respectively. Each of the clamping circuits works to hold an output of a corresponding one of the amplifiers within an operating voltage range of a corresponding one of the A/D converters.

Each of the clamping circuits may be made up of a diode and a constant voltage source. The diode is connected at ends thereof to the output line of a corresponding one of the amplifiers and the constant voltage source generating a constant voltage substantially identical with a maximum operating voltage of a corresponding one of the A/D converters in a forward direction from the output line to the constant voltage source.

Each of the clamping circuits may alternatively include a pnp transistor and a constant voltage source. The pnp transistor is connected at an emitter thereof to the output lines of a corresponding one of the amplifiers and at a base thereof to the reference voltage source. The constant voltage source generates a constant voltage substantially identical with a maximum operating voltage of a corresponding one of the A/D converters. Each of the clamping circuits is so designed that an input voltage appearing at the base of the pnp transistor is identical with a value derived by subtracting a base-emitter voltage drop of the pnp transistor from the constant voltage generated by the constant voltage source.

According to the second aspect of the invention, there is provided a gas concentration measuring apparatus which comprises: (a) a gas concentration sensor equipped with a sensor element made of a solid electrolyte material working to produce an electric signal as a function of concentration of a preselected component of gasses over a given wide gas concentration measuring range; and (b) a sensor circuit including a current-measuring resistor, at least one amplifier, and A/D converters. The sensor circuit works to apply a voltage to the sensor element. The current-measuring resistor functions to measure a current signal flowing through the sensor element produced upon application of the voltage to the sensor element. The amplifier has a predetermined amplification factor and works to amplify the current signal as measured by the current-measuring resistor to output the amplified current signal to one of the A/D converters to determine the concentration of the preselected component of the gasses within one of a plurality of measurement ranges defined within the given wide gas concentration measuring range. The sensor circuit outputs the current signal directly to another of the A/D converters without passing through the amplifier to determine the concentration of the preselected component of the gasses within another of the measurement ranges.

The amplification of the current signal results in expansion of the level of the signal inputted to the A/D converter either to a positive or a negative side, thereby enhancing resolution in determining the concentration of the component of the gasses. The amplifier may have a desired amplification factor thereby enabling the resolution to be enhanced in a desired one of the measurement ranges.

In the preferred mode of the invention, the plurality of measurement ranges include a first measurement range and a second measurement range narrower than the first measurement range. The amplifier serves to produce a narrow range output used to determine the concentration of the preselected component within the second measurement range. The sensor circuit works to output a wide range output directly to the another of the A/D converters to determine the concentration of the preselected component within the first measurement range.

The plurality of measurement ranges may alternatively include an overall measurable range occupying the whole of the given wide gas concentration measuring range and a partial measurable range occupying a portion of the overall measurable range. The amplifier serves to produce the narrow range output used to determine the concentration of the preselected component within the partial measurable range. The sensor circuit works to output the wide range output directly to the another of the A/D converters to determine the concentration of the preselected component within the overall measurable range.

The gas concentration measuring apparatus may further comprise a resistance measuring circuit working to change one of a voltage and a current applied to the sensor element in an ac form and measure one of a resultant change in voltage and a resultant change in current through the current-measuring resistor to determine a resistance of the sensor element.

The sensor element may be so designed that the change in current to determine the resistance of the sensor element is greater than the current signal.

The sensor element may be formed by a lamination of a solid electrolyte plate, a diffusion layer, and an insulating layer which has an oxygen reference chamber defined therein.

The sensor element may be so designed as to measure an air-fuel ratio of a burned gas over the given gas concentration measuring range.

The sensor element may alternatively be formed by a lamination of a pump cell working to pump oxygen into or out of a gas chamber defined in the sensor element filled with the gasses and an oxygen sensor cell working to output a signal as a function of concentration of oxygen contained in the gasses. The sensor circuit controls the pump cell so as to keep the signal outputted by the oxygen sensor cell at a given value.

The sensor circuit also works to produce a voltage as a function of an internal resistance of the sensor element.

The gas concentration sensor may be implemented by an air-fuel ratio sensor designed to measure an air-fuel ratio of a burned gas over the given gas concentration measuring range.

The sensor element may alternatively include a plurality of cells made of a solid electrolyte material, one of which forms a first cell working to pump oxygen into or out of a gas chamber defined in the sensor element filled with the gasses, and another of which forms a second cell working to output a signal as a function of concentration of the preselected component of the gasses into or form which the oxygen is pumped by the first cell.

The amplifier is connected to the current-measuring resistor so that voltage developed across ends of the current-measuring resistor is applied across a positive and a negative terminal of the operational amplifier. The sensor circuit includes a feedback current path for the amplifier and an operational amplifier installed in the feedback current path to absorb a feedback current of the amplifier.

The current-measuring resistor has a first and a second terminal. The sensor circuit also works to apply a fixed reference voltage to the first terminal of the current-measuring resistor, change one of a voltage and a current applied to the sensor element in an ac form, and measure a resultant voltage developed at the second terminal to determine a resistance of the sensor element. The sensor circuit has a switch works to open and close between the second terminal and the amplifier. The switch opens between the second terminal and the amplifier to eliminate a undesirable change in output of the amplifier during determination of the resistance of the sensor element.

The sensor circuit may have a capacitor installed between the switch and the amplifier to hold a voltage developed immediately before the switch is opened.

The sensor circuit may have a clamping circuit disposed in an output line leading to an output terminal of the amplifier. The clamping circuit works to hold an output of the amplifier within an operating voltage range of a corresponding one of the A/D converters.

The clamping circuit may consist of a diode and a constant voltage source. The diode is connected at ends thereof to the output line of the amplifier and the constant voltage source generating a constant voltage substantially identical with a maximum operating voltage of a corresponding one of the A/D converters in a forward direction from the output line to the constant voltage source.

The clamping circuit may alternatively consist of a pnp transistor and a constant voltage source. The pnp transistor is connected at an emitter thereof to the output line of the amplifier and at a base thereof to the reference voltage source. The constant voltage source generates a constant voltage substantially identical with a maximum operating voltage of a corresponding one of the A/D converters. The clamping circuit is so designed that an input voltage appearing at the base of the pnp transistor is identical with a value derived by subtracting a base-emitter voltage drop of the pnp transistor from the constant voltage generated by the constant voltage source.

According to the third aspect of the invention, there is provided a gas concentration measuring apparatus which comprises: (a) a gas concentration sensor equipped with a sensor element made of a solid electrolyte material working to produce an electric signal as a function of a concentration of a preselected component of gasses over a given gas concentration measuring range; and (b) a sensor circuit including a current-measuring resistor, an amplifier, and an A/D converter, the sensor circuit working to apply a voltage to the sensor element. The current-measuring resistor functions to measure a current signal flowing through the sensor element produced upon application of the voltage to the sensor element. The amplifier has a predetermined amplification factor and works to amplify the current signal as measured by the current-measuring resistor to output the amplified current signal to the A/D converter to determine the concentration of the preselected component of the gasses within the given gas concentration measuring range.

The amplification of the current signal results in expansion of the level of the signal inputted to the A/D converter either to a positive or a negative side, thereby enhancing resolution in determining the concentration of the component of the gasses. The amplifier may have a desired amplification factor, thereby enabling the resolution to be enhanced up to a desired degree.

In the preferred mode of the invention, the gas concentration measuring apparatus may further comprise a resistance measuring circuit which works to change one of a voltage and a current applied to the sensor element in an ac form and measure one of a resultant change in voltage and a resultant change in current through the current-measuring resistor to determine a resistance of the sensor element.

The sensor element may be so designed that the change in current to determine the resistance of the sensor element is greater than the current signal.

The sensor element may be formed by a lamination of a solid electrolyte plate, a diffusion layer, and an insulating layer which has an oxygen reference chamber defined therein.

The sensor element may be so designed as to measure an air-fuel ratio of a burned gas over the given gas concentration measuring range.

The sensor element may alternatively be formed by a lamination of a pump cell working to pump oxygen into or out of a gas chamber defined in the sensor element filled with the gasses and an oxygen sensor cell working to output a signal as a function of concentration of oxygen contained in the gasses. The sensor circuit controls the pump cell so as to keep the signal outputted by the oxygen sensor cell at a given value.

The sensor circuit also works to produce a voltage as a function of an internal resistance of the sensor element.

The concentration sensor may be implemented by an air-fuel ratio sensor designed to measure an air-fuel ratio of a burned gas over the given gas concentration measuring range.

The sensor element may consist of a plurality of cells made of a solid electrolyte material, one of which forms a first cell working to pump oxygen into or out of a gas chamber defined in the sensor element filled with the gasses, and another of which forms a second cell working to output a signal as a function of concentration of the preselected component of the gasses into or form which the oxygen is pumped by the first cell.

The amplifier is connected to the current-measuring resistor so that voltage developed across ends of the current-measuring resistor is applied across a positive and a negative terminal of the operational amplifier. The sensor circuit may include a feedback current path for the amplifier and an operational amplifier installed in the feedback current path to absorb a feedback current of the amplifier.

The current-measuring resistor has a first and a second terminal. The said sensor circuit works to apply a fixed reference voltage to the first terminal of the current-measuring resistor, change one of a voltage and a current applied to the sensor element in an ac form, and measure a resultant voltage developed at the second terminal to determine a resistance of the sensor element. The sensor circuit has a switch working to open and close between the second terminal and the amplifier. The switch opens between the second terminal and the amplifier to eliminate a undesirable change in output of the amplifier during determination of the resistance of the sensor element.

The sensor circuit may have a capacitor installed between the switch and the amplifier to hold a voltage developed immediately before the switch is opened.

The sensor circuit may have a clamping circuit disposed in an output line leading to an output terminal of the amplifier. The clamping circuit works to hold an output of the amplifier within an operating voltage range of the A/D converter.

The clamping circuit may be made up of a diode and a constant voltage source. The diode is connected at ends thereof to the output line of the amplifier and the constant voltage source generating a constant voltage substantially identical with a maximum operating voltage of the A/D converters in a forward direction from the output line to the constant voltage source.

The clamping circuit may alternatively consist of a pnp transistor and a constant voltage source, the pnp transistor is connected at an emitter thereof to the output line of the amplifier and at a base thereof to the reference voltage source. The constant voltage source generates a constant voltage substantially identical with a maximum operating voltage of the A/D converter. The clamping circuit is so designed that an input voltage appearing at the base of the pnp transistor is identical with a value derived by subtracting a base-emitter voltage drop of the pnp transistor from the constant voltage generated by the constant voltage source.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
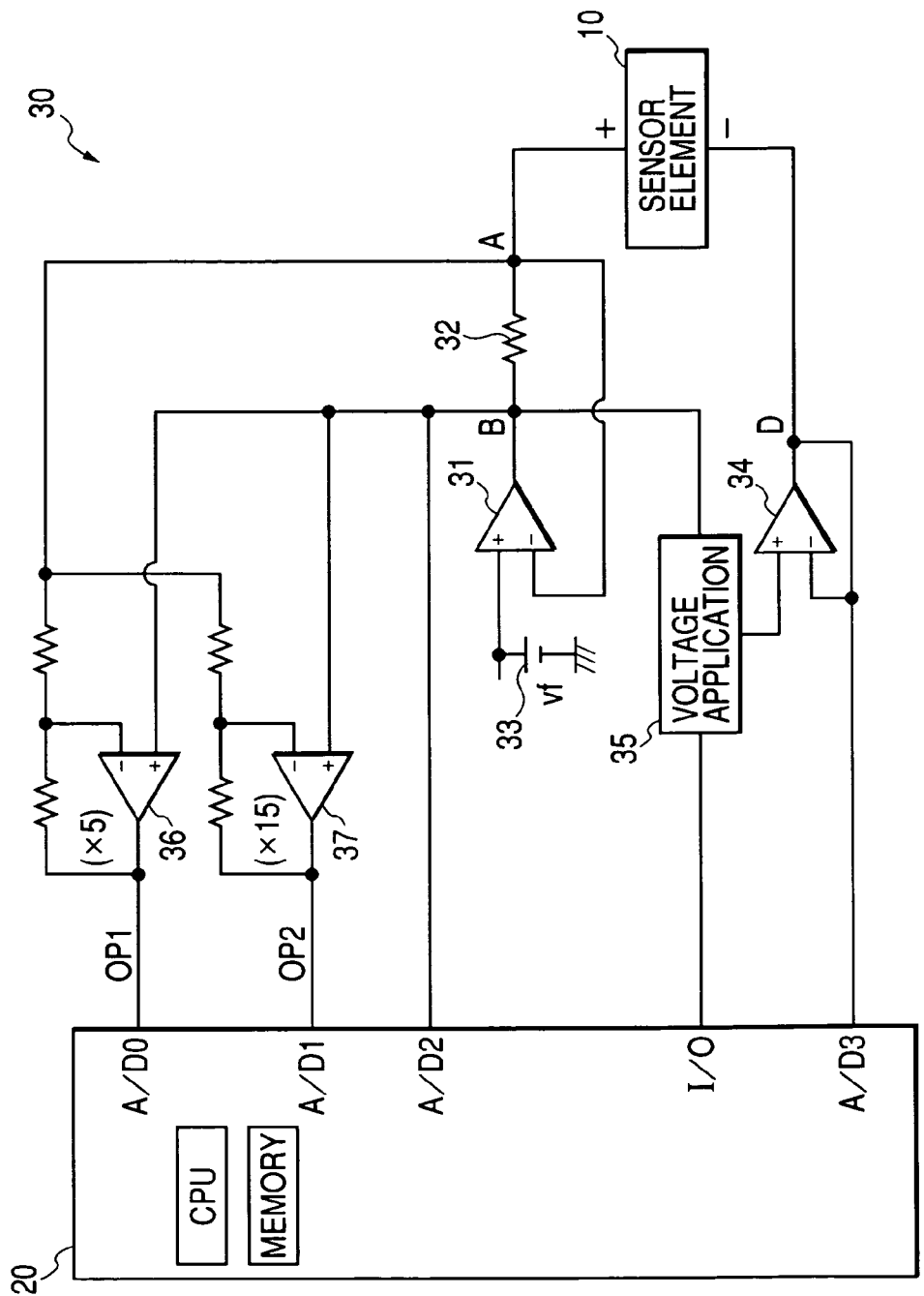
FIG. 1 is a circuit diagram which shows an electric structure of a gas concentration measuring apparatus according to the first embodiment of the invention.

Referring to the drawings, wherein like reference numbers refer to like parts in several views, particularly to FIG. 1, there is shown a gas concentration measuring apparatus designed to measure the concentration of oxygen ($O_2$) contained in exhaust emissions of automotive engines as indicating an air-fuel ratio. The measured concentration is used in an air-fuel ratio control system consisting of an engine ECU etc. The air-fuel ratio control system works to perform a stoichiometric burning control to bring the air-fuel ratio near the stoichiometric air-fuel ratio under feedback control and a lean-burn control to bring the air-fuel ratio to within a given lean range under feedback control. The gas concentration measuring apparatus is designed to measure the air-fuel ratio over a wide range of from a fuel-rich zone (e.g., an air-fuel ratio of 11) to an atmospheric zone (i.e., a fuel-free zone) in order to meet emission regulations or on-board diagnostic (OBD) requirements which have been increasingly tightened or to purge a NOx occluding/reducing catalyst of NOx emissions which is installed typically in an exhaust system of lean burn engines and to minimize the degree to which sulfur contained in fuel poisons the NOx occluding/reducing catalyst.

The gas concentration measuring apparatus includes a microcomputer 20, a sensor control circuit 30, and an oxygen sensor 10 (will be referred to as an air-fuel (A/F) sensor below) which works to produce a current signal as a function of concentration of oxygen contained in exhaust emissions introduced into a gas chamber formed in the A/F sensor 10.

Figure 2:
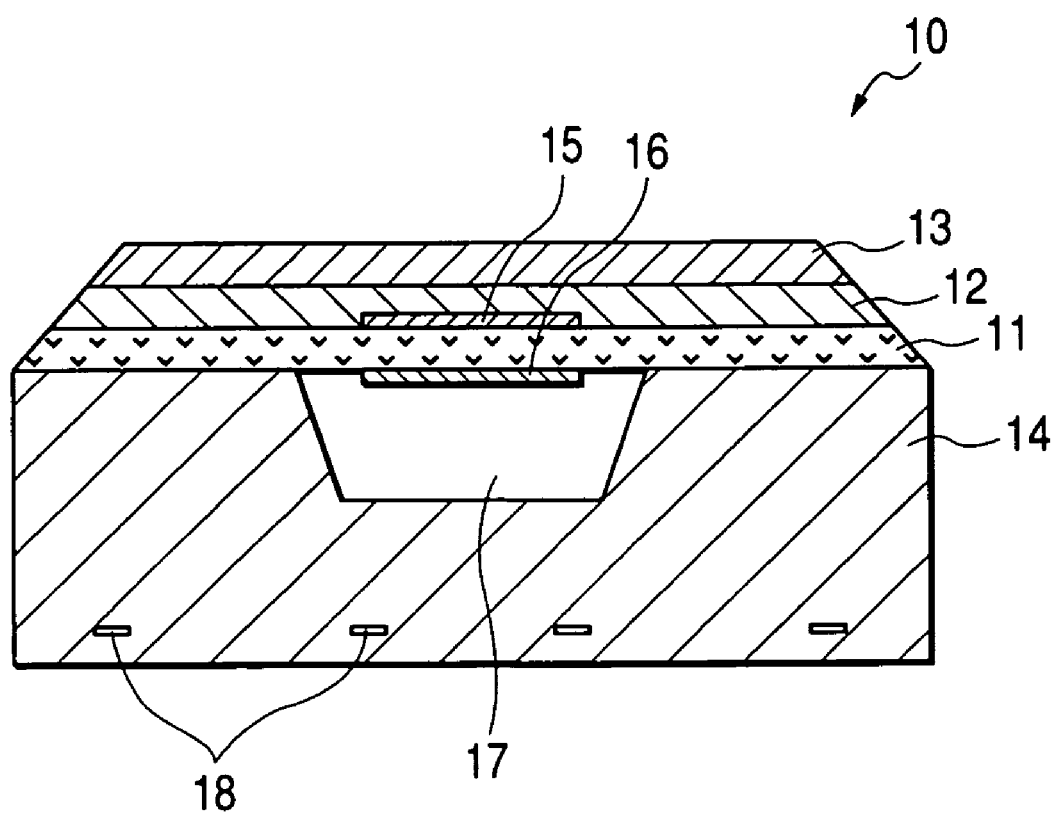
FIG. 2 is a transverse sectional view which shows a sensor element used in the gas concentration measuring apparatus as illustrated in FIG. 1.

The A/F sensor 10 includes a laminated sensor element 10 which has a sectional structure, as illustrated in FIG. 2. The sensor element 10 has a length extending perpendicular to the drawing surface of FIG. 2 and is, in practice, disposed within a sensor housing and a protective cover. The A/F sensor 10 is installed in an exhaust pipe of the engine. For instance, EP0 987 546 A2, assigned to the same assignee as that of this application teaches a structure and control of an operation of this type of gas sensor in detail, disclosure of which is incorporated herein by reference.

The sensor element 10 is made up of a solid electrolyte layer 11, a diffusion resistance layer 12, a shielding layer 13, and an insulating layer 14 which are laminated vertically as viewed in the drawing. The sensor element 10 is surrounded by a protective layer (not shown). The solid electrolyte layer 11 is made of a rectangular partially-stabilized zirconia sheet and has upper and lower electrodes 15 and 16 affixed to opposed surfaces thereof. The diffusion resistance layer 12 is made of a porous sheet which permits exhaust gasses to flow onto the electrode 15. The shielding layer 13 is made of a dense sheet which inhibits the exhaust gasses from passing therethrough. The layers 12 and 13 are each formed using a sheet made of ceramic such as alumina, spinel, or zirconia and have average porosities, or gas permeability different from each other.

The insulating layer 14 is made of a high-temperature conductive material such as ceramic and has formed therein an air duct 17 to which the electrode 16 is exposed. The insulating layer 14 has a heater 18 embedded therein. The heater 18 is made of heating wire which is supplied with power from a storage battery installed in the vehicle to produce heat the whole of the sensor element 10 up to a desired activatable temperature.

The exhaust gasses flowing within an exhaust pipe of the engine to which the sensor element 10 is exposed enter and pass through the side of the diffusion resistance layer 12 and reaches the electrode 15. When the exhaust gasses are lean, oxygen molecules contained in the exhaust gasses are decomposed or ionized by the electrode 15, so that they are discharged to the air duct 17 through the electrode 16. Alternatively, when the exhaust gasses are richer than a predetermined value, oxygen molecules contained in air within the air duct 17 are ionized by the electrode 16 so that they are discharged into the exhaust pipe through the electrode 15.

Figure 3:
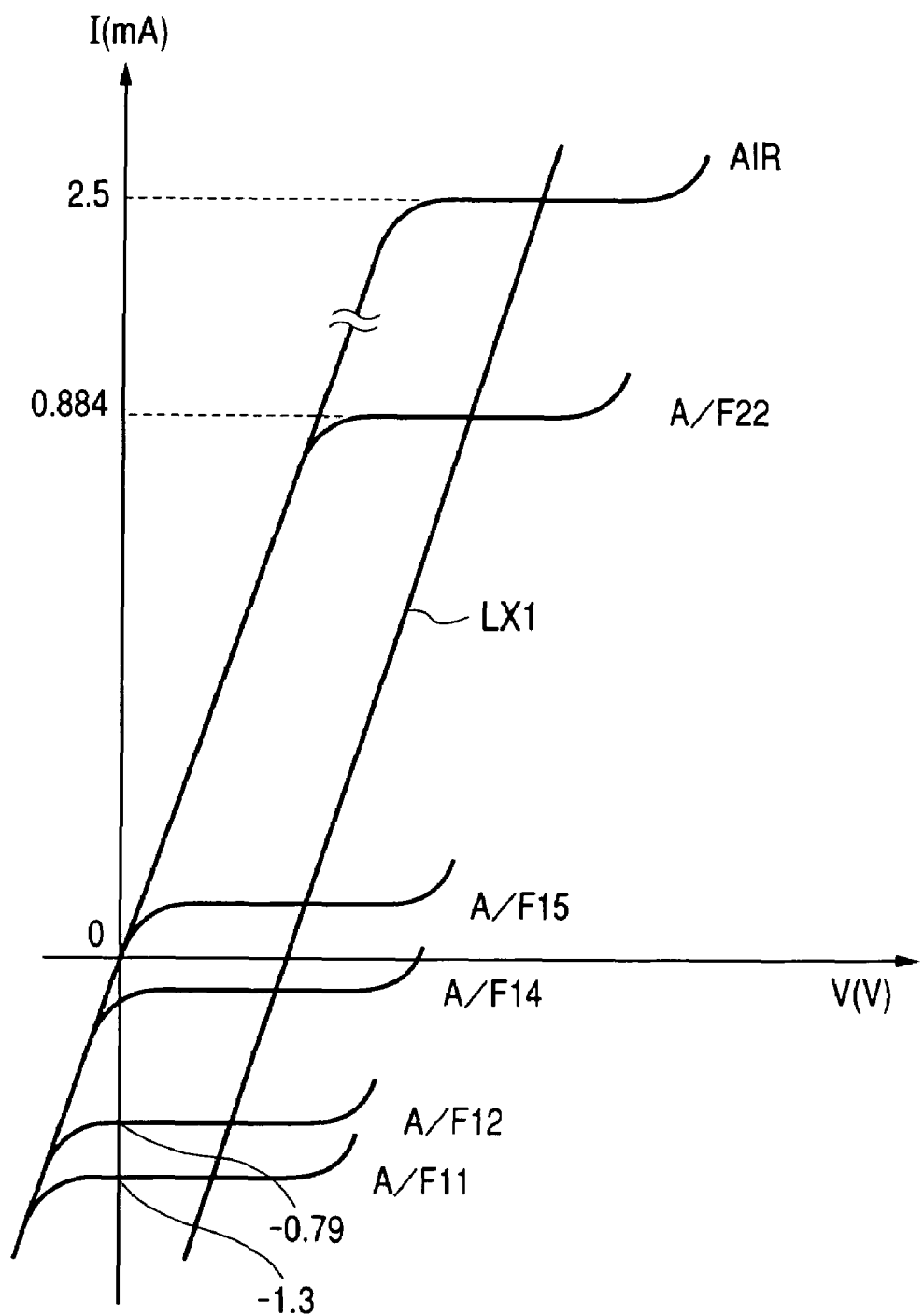
FIG. 3 shows an example of an applied voltage-to-output current map for use in determining a target voltage to be applied to the sensor element as illustrated in FIG. 2.

FIG. 3 shows a voltage-to-current relation (i.e., V-I characteristic) of the A/F sensor. Straight segments of curves extending parallel to the abscissa axis (i.e., V-axis) indicate limiting current ranges within which the sensor element 10 produces an electric current (i.e., a limiting current) as a function of an air-fuel ratio (i.e., richness or leanness). Specifically, as the air-fuel ratio is changed to the lean side, the current produced by the sensor element 10 increases, while as the air-fuel ratio is changed to the rich side, the current produced by the sensor element 10 decreases. A line LX1 indicates a target voltage to be applied to the sensor element 10 (i.e., the electrodes 15 and 16). An inclination of the line LX1 is identical substantially with that of a resistance-dependent line as illustrated on left side of the drawing.

In this embodiment, a range of an A/F ratio=11 to an air-fuel ratio within the atmospheric air (i.e., the free-air ratio) is defined as an air-fuel ratio measuring range. The sensor element 10 is so designed as to produce −1.3 mA when an A/F ratio is 11 and 2.5 mA when the exhaust gasses corresponds to the air. These current values are one-tenth of those produced by the cup-shaped A/F sensor, as described in the introductory part of this application.

Figure 4:
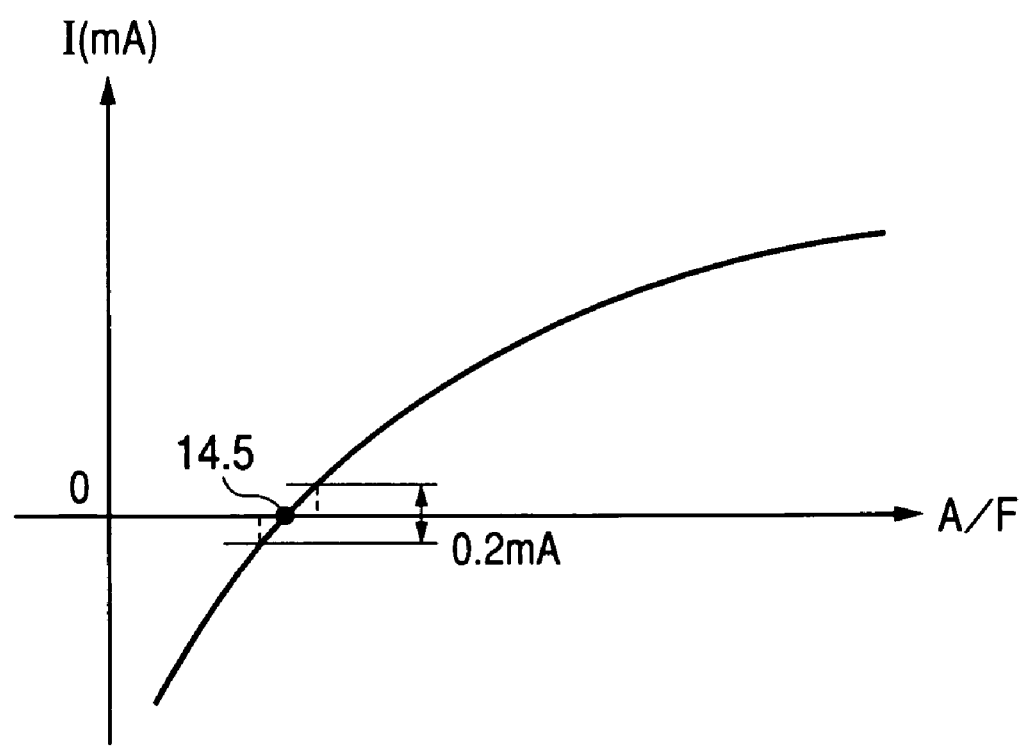
FIG. 4 is a graph which illustrates a relation between an air-fuel ratio and the current produced by the sensor element as illustrated in FIG. 2.

FIG. 4 is a graph which illustrates a relation between the A/F ratio and the current I produced by the sensor element 10. The graph shows that as the A/F ratio is shifted to the lean side, a current change per unit of A/F ratio (i.e. the inclination of a curve) decreases. When the A/F ratio is around a stoichiometric air-fuel ratio (A/F=14.5), a current change of 0.2 mA arises which corresponds to A/F ratio of one (1) and is approximately one-tenth of that in the cup-shaped A/F sensor.

Referring back to FIG. 1, the gas concentration measuring apparatus, as described above, includes the microcomputer 20 and the sensor control circuit 30 and works to determine the A/F ratio and an impedance Zac of the sensor element 10 (will also be referred to as a sensor element impedance below) based on an output of the sensor element 10.

The microcomputer 20 is made of a known arithmetic unit consisting of a CPU, memories, A/D converters, an I/O port, etc. which works to receive through the A/D converters analog current signals produced by the sensor control circuit 30 as a function of the output of the sensor element 10 and calculate the A/F ratio and the sensor element impedance Zac. The A/D converters have a resolution of 10 bits, for example, and operate within a range of 0 to 5V. The A/F ratio, as calculated in the microcomputer 20, is outputted to an engine ECU (not shown) for use in air-fuel ratio feedback control.

The sensor control circuit 30 includes an operational amplifier 31, a current-measuring resistor 32, a reference voltage source 33, an operational amplifier 34, an voltage application control circuit 35, and operational amplifiers (differential amplifiers) 36 and 37. The reference voltage source 33 is connected to a positive (+) terminal of the sensor element 10 through the operational amplifier 31 and the current-measuring resistor 32. The voltage application control circuit 35 is connected to a negative (−) terminal of the sensor element 10 through the operational amplifier 34. The voltage appearing at a junction A (also referred to as a first terminal below) leading to an end of the resistor 32 is kept identical with the reference voltage Vf. The sensor element current (i.e., an output of the sensor element 10) flows through the current-measuring resistor 32 to change the voltage appearing at a junction B (also referred to as a second terminal). For instance, when the exhaust gasses are on the lean side, the current flows from the positive terminal to the negative terminal of the sensor element 10, so that the voltage appearing at the second terminal B rises. Alternatively, when the exhaust gasses are on the rich side, the current flows from the negative terminal to the positive terminal of the sensor element 10, so that the voltage appearing at the second terminal B drops. The voltage application control circuit 35 works to monitor the voltage at the second terminal B and determine a target voltage to be applied to the sensor element 10 as a function of the monitored voltage, for example, by look-up using the target applying voltage line LX1, as illustrated in FIG. 3. The voltage application control circuit 35 controls the voltage appearing at a junction D, as will also be referred to as a third terminal below, based on the target voltage through the operational amplifier 34. However, in a case where it is required to determine the A/F ratio within a range near the stoichiometric air-fuel ratio, the voltage application control circuit 35 may fix the voltage to be applied to the sensor element 10.

To the first and second terminals A and B of the current-measuring resistor 32, the operational amplifiers 36 and 37 are coupled, respectively. Outputs OP1 and OP2 of the operational amplifiers 36 and 37 are inputted to the A/D converters A/D0 and A/D1 of the microcomputer 20, respectively. The operational amplifiers 36 and 37 are arranged in a parallel relation to each other. The operational amplifier 36 has an amplification factor of five (5). The operational amplifier 37 has an amplification factor of fifteen (15). The operational amplifiers 36 and 37 are driven by the battery. The outputs OP1 and OP2 of the operational amplifiers 36 and 37 (i.e., a current signal produced by the sensor element 10) are used as A/F ratio determining signals to determine the A/F ratio in the microcomputer 20. Specifically, the microcomputer 20 uses the two signals (i.e., the outputs OP1 and OP2) to determine the A/F ratio.

The operational amplifier 36 is so designed as to produce the output OP1 which enables the A/F ratio to be determined over an A/F measuring range of, for example, an A/F=11 to the free-air ratio. The operational amplifier 37 is so designed as to produce the output OP2 which enables the A/F ratio to be determined within a limited range of, for example, an A/F=12 to an A/F=22 including the stoichiometric air-fuel ratio. In the following discussion, the output OP1 will also be referred to as a wide range measuring signal. The output OP2 will also be referred to as a narrow range measuring signal or a stoichiometric air-fuel ratio measuring signal.

The microcomputer 20 works to sweep the voltage applied to the sensor element 10 instantaneously to determine the sensor element impedance Zac as a function of a resultant change in current produced by the sensor element 10. Specifically, the voltage application control circuit 35 is responsive to a command signal from the microcomputer 20 to change the voltage applied to the sensor element 10 (i.e., the voltage at the terminal D) by a given level (e.g., 0.3V) to the positive and negative sides. The microcomputer 20 monitors a resultant change in voltage at the terminal D through the A/D converter A/D3. The voltage at the second terminal B is also changed following the change in voltage at the terminal D as a function of the impedance Zac of the sensor element 10. The microcomputer 20 also monitors the change in voltage at the second terminal B through the A/D converter A/D2 and divides the change $\Delta V$ in the voltage at the terminal D by $\Delta I$ that is derived by dividing the change in voltage at the second terminal B by a resistance value of the current-measuring resistor 32 to determine the sensor element impedance Zac ($=\Delta V/\Delta I$). The determination of the sensor element impedance Zac may alternatively be made by supplying the current to the sensor element 10, sweeping it in an ac form, and monitoring a resultant change in current or voltage produced in the sensor element 10. U.S. Pat. No. 6,578,563 B2, issued Jun. 17, 2003, assigned to the same assignees as that of this application teaches how to determine the sensor element impedance Zac, disclosure of which is incorporated herein by reference.

The determination of the sensor element impedance Zac is performed at an regular time interval. Specifically, the microcomputer 20 outputs an impedance measuring command signal to the voltage application control circuit 35 cyclically. The microcomputer 20 also works to control an electric power supplied to the heater 18 so as to keep the sensor element impedance Zac at a given target value in order to maintain the sensor element 10 in a desired activatable condition where the sensor element 10 produces an output as a function of the A/F ratio correctly.

The resolution of the sensor control circuit 30 in determining the A/F ratio will be evaluated below.

The A/F measuring range of the gas concentration measuring apparatus is, as described above, between an A/F ratio of 11 and the free-air ratio. The sensor element 10 and the sensor control circuit 30 are so constructed as to meet the following electric specifications. When the exhaust gasses show the free-air ratio, the sensor element 10 produces a current of 2.5 mA. When the A/F ratio is 11, the sensor element 10 produces a current of −1.3 mA. When the A/F ratio is 12, the sensor element 10 produces a current of −0.79 mA. When the A/F ratio is 22, the sensor element 10 produces a current of 0.884 mA. The ac impedance Zac is 28Ω. A voltage change produced to measure the impedance Zac is ±0.3V. A current measuring resistance is 185Ω. The reference voltage Vf is 2.5V. The operational amplifiers 36 and 37 are driven by a single power supply and clamped at 5V, so that they produce an output only within a range of 0 to 5V.

The operational amplifier 36 is, thus, designed to have an A/F measuring range of an A/F ratio of 11 to the free-air ratio and produce outputs, as shown below, at the free-air ratio and an A/F ratio of 11, respectively.

$$OP1=2.5V+185\Omega\times 2.5\text{ mA}\times 5=4.8125V$$

$$OP1=2.5V+185\Omega\times(-1.3\text{ mA})\times 5=1.2975V$$

The operational amplifier 37 is designed to have an A/F measuring range of A/F ratios of 12 to 22 and produce outputs, as shown below, when the A/F ratio is 22 and 11, respectively.

$$OP2=2.5V+185\Omega\times 0.884\text{ mA}\times 15=4.9531V$$

$$OP2=2.5V+185\Omega\times(-0.79\text{ mA})\times 15=0.30775V$$

Specifically, within the A/F measuring range of an A/F ratio of 11 to the free-air ratio, the output OP1 of the operational amplifier 36 falls within an operational voltage range (0 to 5V) of the A/D converter A/D0. The operational amplifier 36 is, thus, capable of outputting a signal precisely within the wider A/F ratio measuring range. Within the A/F measuring range of A/F ratios of 11 to 22, the output OP2 of the operational amplifier 37 falls within an operational voltage range (0 to 5V) of the A/D converter A/D1. The operational amplifier 37 is, thus, capable of outputting a signal precisely within the limited A/F ratio measuring range defined across the stoichiometric air-fuel ratio.

In a case where the A/D converters A/D0 and A/D1 are each implemented by a 10-bit A/D converter, the A/F ratio measurement resolution within the range of an A/F of 11 to the free-air ratio is expressed below on the above numerical conditions.

$$(4.8125-1.2975)/5V\times 1024=720$$

Figure 16:
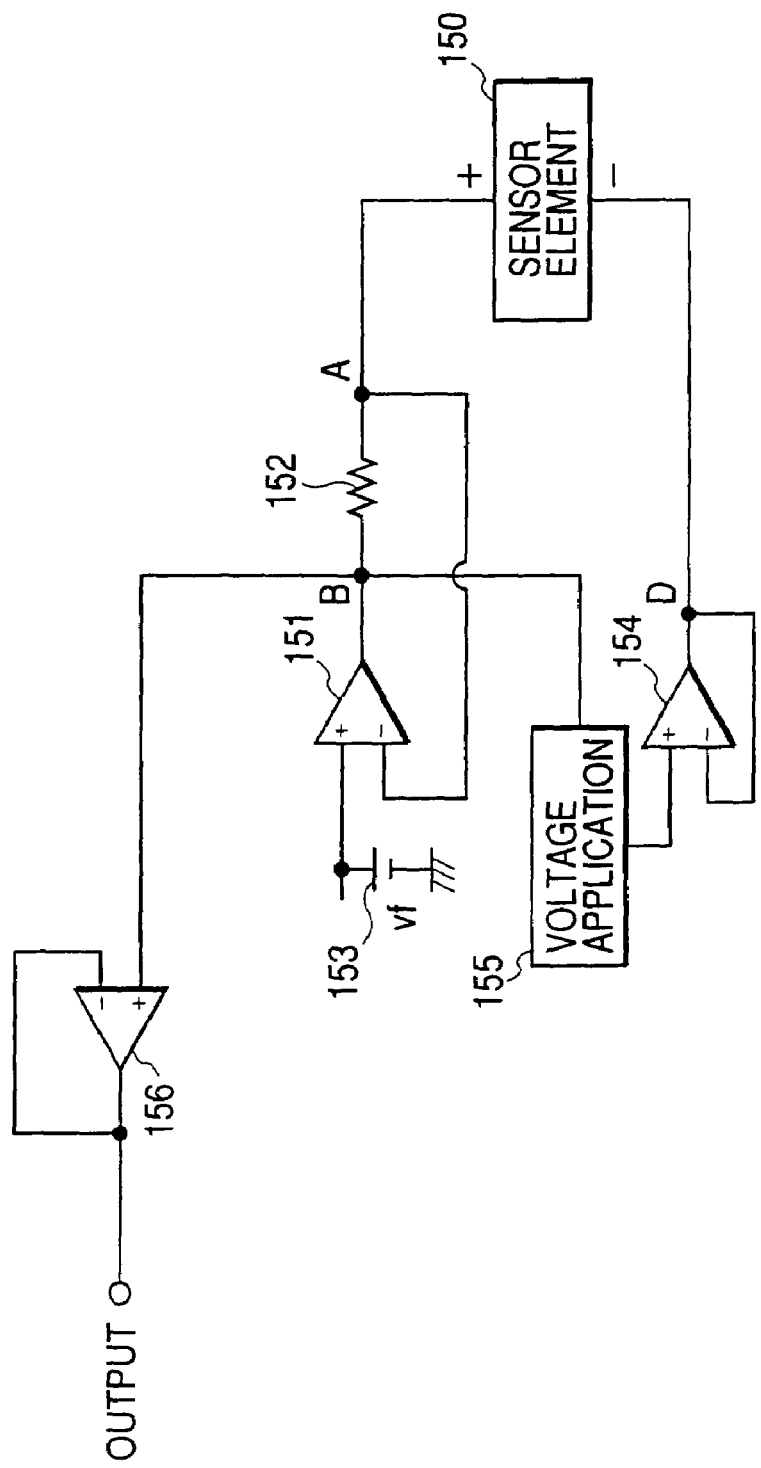
FIG. 16 is a circuit diagram which shows an example of a conventional sensor control circuit.
Figure 17:
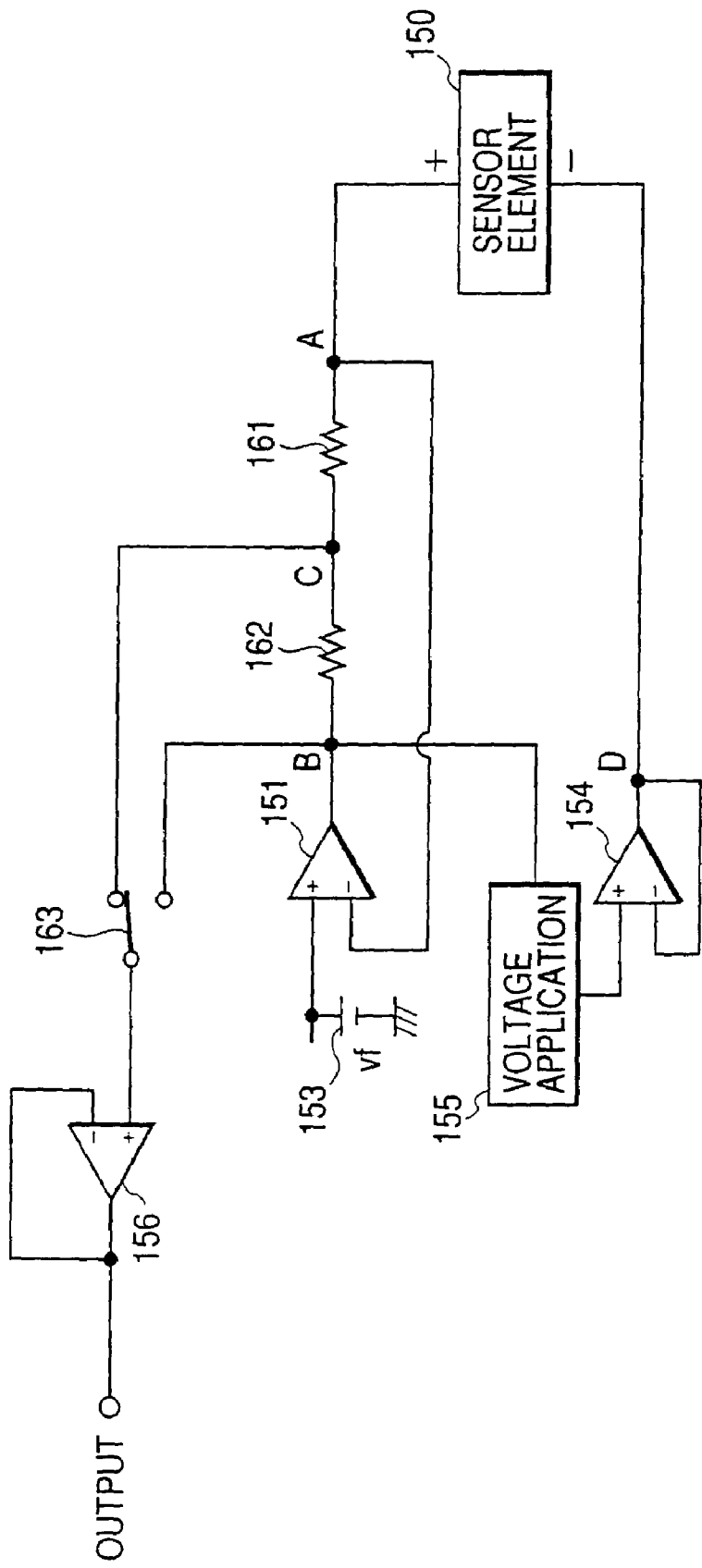
FIG. 17 is a circuit diagram which shows another example of a conventional sensor control circuit.

It is found that the A/F ratio measurement resolution is five times (720/144=5) greater than that in the conventional structure, as illustrated in FIG. 16.

If a current change corresponding to an A/F ratio of one (1) in the vicinity of the stoichiometric air-fuel ratio is 0.2 mA, the A/F ratio measurement resolution is $$0.2\text{ mA}\times 185\Omega\times 15/5V\times 1024=114$$

In this case, the resolution will be 0.009A/F per LSB which meets a condition required in high-resolution control in the vicinity of the stoichiometric air-fuel ratio where the resolution should be less than, for example, 0.01A/F.

The sensor element impedance Zac is, as described above, determined using changes in voltage at the second terminal B and the terminal D, as illustrated in FIG. 1. The sensor control circuit 30 is so designed that the voltages developed at the terminal B and terminal D during the determination of the impedance Zac may lie within the operational voltage range (0 to 5V) of the A/D converters A/D2 and A/D3. Specifically, when the exhaust gasses show the free-air ratio and an A/F ratio of 11 at the time of measurement of the impedance Zac, the voltage appearing at the second terminal B has values, as shown below, resulting from a change in voltage at the terminal D to the positive side which is less than a maximum operating voltage of the A/D converter A/D2.

Voltage at $B=2.9625V+185\Omega \times (0.3V/28\Omega)=4.9446V$

Voltage at $B=2.2595V+185\Omega \times (0.3V/28\Omega)=4.2416V$

When the voltage appearing at the terminal B is changed to the negative side with a change in voltage appearing at the terminal D to the negative side, the voltage at the terminal B has the following minimum value (when the A/F ratio is 11).

Voltage at $B=2.2595V+185\Omega \times (-0.3V/28\Omega)=0.2774V$

Specifically, when the voltage at the terminal D is swept to the positive and negative sides to measure the impedance Zac, a resultant voltage developed at the terminal B lies within the operational voltage range (0 to 5V) of the A/D converter A/D2. This enables high-resolution measurement of the impedance Zac.

The gas concentration measuring apparatus of this embodiment provides the following effects.

The current signal produced from the sensor element 10 and passed through the current-measuring resistor 32 is amplified by the operational amplifiers 36 and 37 having different amplification factors and then inputted to the microcomputer 20 through the A/D converters A/D0 and A/D1. The levels of signals inputted to the A/D converters A/D0 and A/D1 are expanded either to the positive or negative potential side, thereby resulting in improved resolution in determining the A/F ratio. The operational amplifiers 36 and 37 are provided for the two different A/F ratio measuring ranges, thus permitting amplification to be achieved which is suitable for each of the ranges, which results in improved accuracy of measuring the A/F ratio over a desired wider rich-to-lean range. The accuracy or resolution in determining the A/F ratio may be changed in each of the two A/F ratio measuring ranges.

The gas concentration measuring apparatus of this embodiment is suitable especially for use of a laminated sensor element. Specifically, the sensor element 10 is, as described above, of a laminated structure in which a change in current produced in the sensor element 10 when the impedance Zac is measured is greater than that when the A/F ratio is measured, thus resulting in imbalance of the current. Also in this case, however, the gas concentration measuring apparatus of this embodiment is capable of keeping the desired resolution in determining the A/F ratio within each of the A/F ratio measuring ranges.

The operational amplifier 37 provided for the limited A/F ratio measuring range of A/F ratios 12 to 20 lying within the wide A/F ratio measuring range of an A/F ratio of 11 to the free-air ratio has an increased amplification factor, thus resulting in improved resolution in determining the A/F ratio within the limited A/F ratio measuring range. Specifically, the limited A/F ratio measuring range includes the stoichiometric air-fuel ratio, therefore, the A/F ratio measurement resolution in the vicinity of the stoichiometric air-fuel ratio is improved, thereby enabling high-resolution stoichiometric air-fuel ratio control.

In a case where the operation amplifier 37 whose amplification factor is 15 is employed, the output OP2 thereof has values, as shown below, at the free-air ratio and an A/F ratio of 11, respectively.

$OP2=2.5V+185\Omega \times 2.5\ mA \times 15=9.4375V$ $OP2=2.5V+185\Omega \times (-1.3\ mA) \times 15=-1.1075V$ The above values are out of the 0-to-5V operational voltage range of the A/D converter A/D1. The operational amplifier 37 is powered by the battery installed in the vehicle, so that it cannot output a negative voltage. In order to avoid this problem, the gas concentration measuring apparatus of this embodiment is designed to have two A/F ratio-measuring channels. Specifically, the operational amplifier 37 serves to keep high resolution in determining the A/F ratio within the limited A/F ratio measuring range, while the operational amplifier 36 serves to keep high resolution within a range extending outside the limited A/F ratio measuring range covered by the operational amplifier 37.

Figure 5:
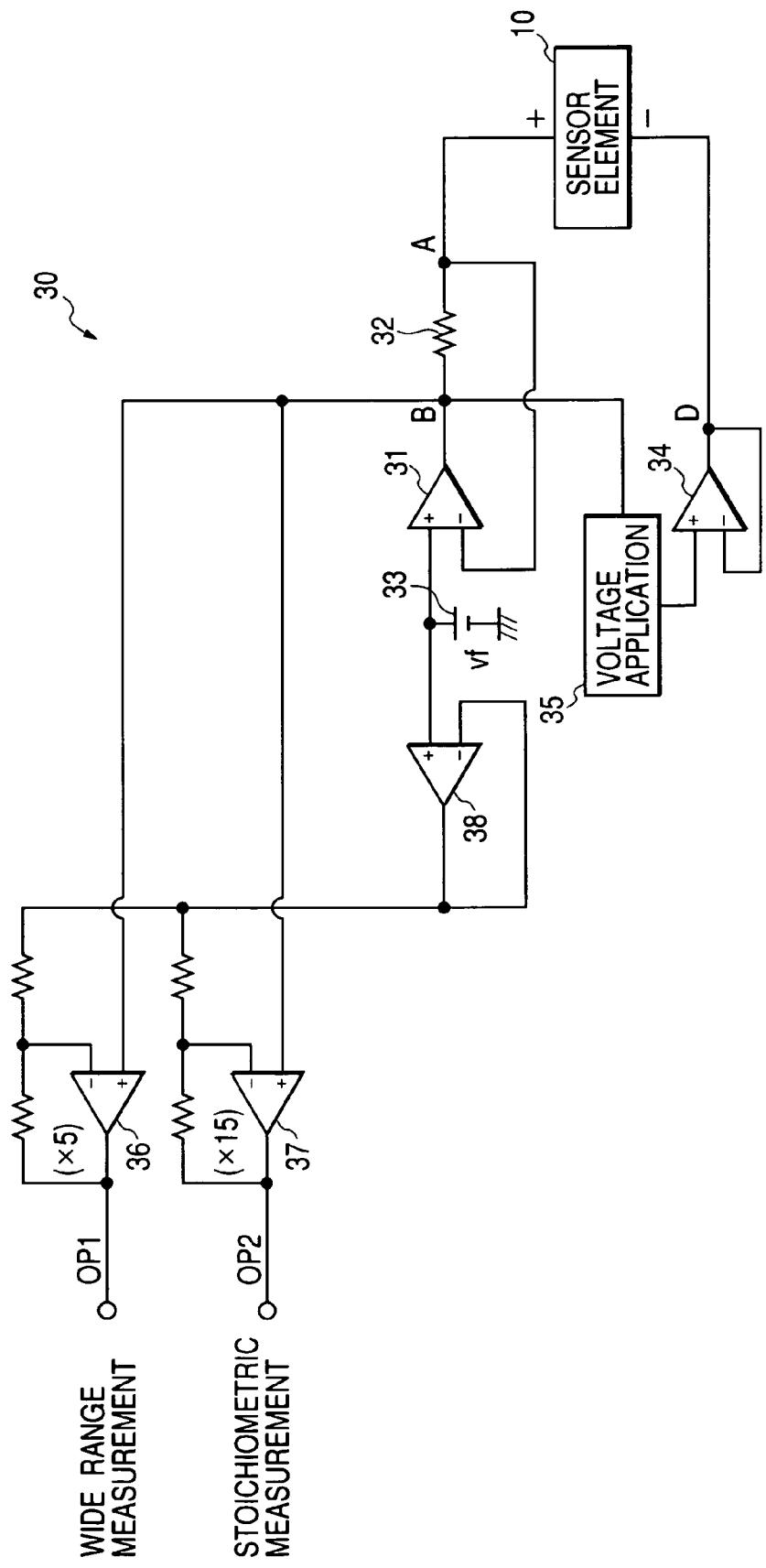
FIG. 5 is a circuit diagram which shows a first modification of a sensor control circuit.
Figure 6:
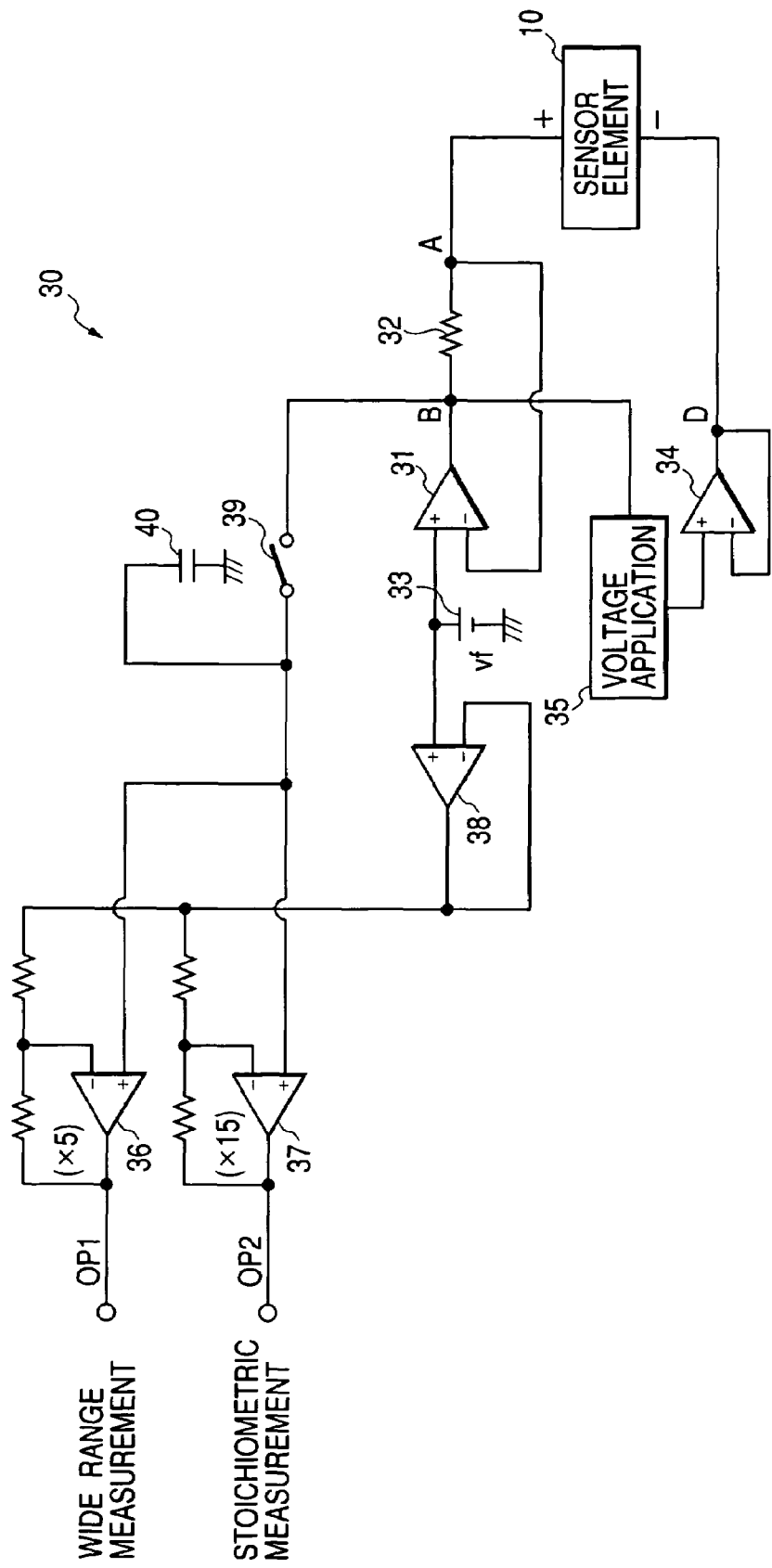
FIG. 6 is a circuit diagram which shows a second modification of a sensor control circuit.

The sensor control circuit 30 may be modified as illustrated in FIG. 5 or 6. The connections of the terminal B and the terminal D to the microcomputer 20 are identical with those in FIG. 1, and illustration thereof will be omitted here.

In the structure in FIG. 1, a potential difference across the current-measuring resistor 32, that is, between the terminals A and B is amplified by the operational amplifiers 36 and 37, respectively. In the structure in FIG. 5, the operational amplifiers 36 and 37 are so designed as to amplify a potential difference between the reference voltage Vf and the voltage appearing at the terminal B. Specifically, the voltage at the terminal A is identical with the reference voltage Vf. The sensor control circuit 30 is, thus, so designed that the reference voltage Vf is inputted to the operational amplifiers 36 and 37 through the operational amplifier 38.

In the structure in FIG. 1, the outputs of the operational amplifiers 36 and 37 are fedback to the terminal A, so that fedback currents flow through the current-measuring resistor 32, which may result in an error in determining the A/F ratio. In the structure in FIG. 5, the operational amplifier 38 is disposed in a current feedback line to absorb the feedback currents of the operational amplifiers 36 and 37, thereby eliminating the above error to keep the desired resolution in determining the A/F ratio. Typically, the reference voltage Vf is provided by a fraction of voltage across two resistors. In this case, the feedback currents of the operational amplifiers 36 and 37 will result in an undesirable change in reference voltage Vf. In order to eliminate such a voltage change, the operational amplifier 38 is installed in the current feedback line. However, in a case where the reference voltage Vf can be sunk and sourced, it is possible to remove the operational amplifier 38 from the sensor control circuit 30.

The sensor control circuit 30, as shown in FIG. 6, includes a switch 39. The switch 39 is disposed between the terminal B and the operational amplifiers 36 and 37. The switch 39 is turned off or opened when it is required to measure the impedance Zac. Specifically, a sweep of the voltage applied to the sensor element 10 to measure the impedance Zac will cause the current flowing through the current-measuring resistor 32 to change, which leads to an undesirable change in outputs of the operational amplifiers 36 and 37, thus resulting in an error in determining the A/F ratio. Therefore, when it is required to measure the impedance Zac, the switch 39 is opened to eliminate such an error.

The sensor control circuit 30 may be equipped with a capacitor 40. The capacitor 40 works to hold the level of the current signal produced by the sensor element 10 immediately before the switch 39 is opened, that is, before the impedance Zac is measured. This enables determination of the A/F ratio even during measurement of the impedance Zac.

Figure 7:
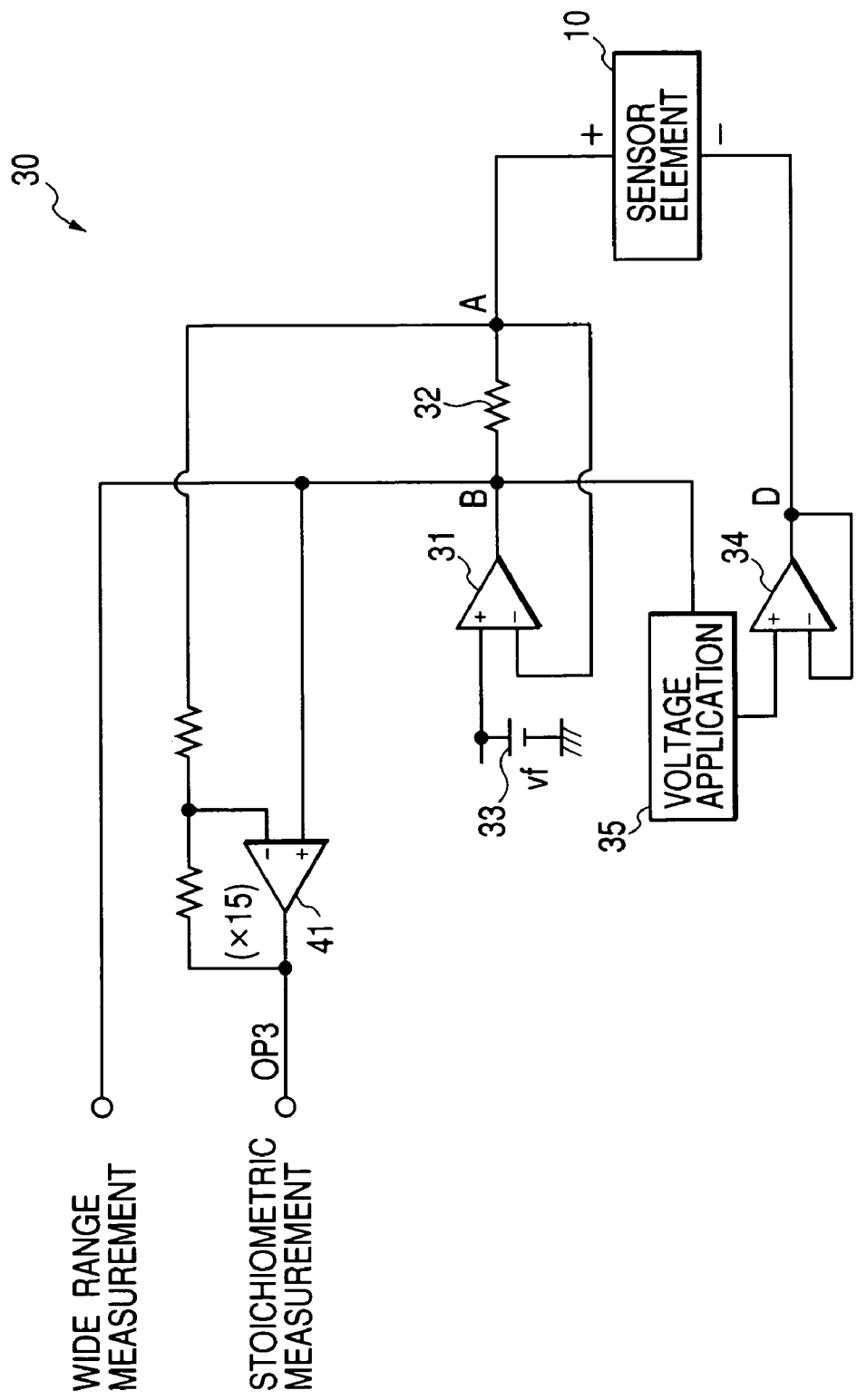
FIG. 7 is a circuit diagram which shows an electric structure of a sensor control circuit of a gas concentration measuring apparatus according to the second embodiment of the invention.

FIG. 7 shows the sensor control circuit 30 according to the second embodiment of the invention which is similar to that of the first embodiment in use of the two channels in outputting the A/F ratio determining signals to the microcomputer 20, but different therefrom in that an operational amplifier is installed only in one of the two channels.

Specifically, a signal produced by the sensor element 10 (i.e., the wide range measuring signal outputted to the A/D converter A/D0 in FIG. 1) is outputted directly to the microcomputer 20 through one of the channels used in determining the A/F ratio over the wide A/F ratio measuring range, while a signal (i.e., the stoichiometric air-fuel ratio measurable signal outputted to the A/D converter A/D1 in FIG. 1) is outputted to the microcomputer 20 through an operational amplifier 41 in the other channel used in determining the A/F ratio within the limited A/F ratio measuring range. The amplification factor of the operational amplifier 41 is fifteen (15).

The resolution of the sensor control circuit 30 in determining the A/F ratio will be evaluated below.

The A/F measuring range of the sensor control circuit 30 of this embodiment is, like the first embodiment, between an A/F ratio of 11 and the free-air ratio. Other electrical specifications of the sensor element 10 and the sensor control circuit 30 are the same as those in the first embodiment.

The wide range measuring signal is provided by the voltage appearing at the terminal B which has values, as shown below, at the free-air ratio and an air-fuel ratio of 11, respectively.

Voltage at $B=2.5V+185\Omega \times 2.5$ mA$=2.9625V$

Voltage at $B=2.5V+185\Omega \times (-1.3$ mA$)=2.2595V$

The operational amplifier 41 is designed to have an A/F measuring range of A/F ratios of 12 to 22 and produce an output OP3 which has values, as shown below, when the A/F ratio is 22 and 11, respectively.

$OP3=2.5V+185\Omega \times 0.884$ mA$\times 15=4.9531V$ $OP3=2.5V+185\Omega \times (-0.79$ mA$)\times 15=0.30775V$ Specifically, the signal outputted from the sensor control circuit 30 directly to the microcomputer 20 without any operational amplifier falls within the operational voltage range (0 to 5V) of the A/D converter A/D0, thus ensuring high resolution in determining the wide A/F ratio measuring range. The signal outputted from the sensor control circuit 30 through the operational amplifier 41, that is, the output OP3 also falls within the operational voltage range (0 to 5V) of the A/D converter A/D1, thus ensuring high resolution in determining the A/F ratio within the limited A/F ratio measuring range across the stoichiometric air-fuel ratio.

In a case where the A/D converters A/D0 and A/D1 are each implemented by a 10-bit A/D converter, the A/F ratio measurement resolution within the range of an A/F of 11 to the free-air ratio is expressed below on the numerical conditions as described in the first embodiment.

$(2.9625-2.2595)/5V\times 1024=144$

Specifically, the A/F ratio measurement resolution substantially identical with that in the structure of FIG. 16.

If a current change corresponding to an A/F ratio of one (1) in the vicinity of the stoichiometric air-fuel ratio is 0.2 mA, the A/F ratio measurement resolution is $0.2$ mA$\times 185\Omega \times 15/5V\times 1024=114$ In this case, the resolution will be 0.009A/F per LSB which meets a condition required in high-resolution control in the vicinity of the stoichiometric air-fuel ratio where the resolution should be less than, for example, 0.0A/F.

The sensor element impedance Zac is, like the first embodiment, determined using changes in voltage at the terminals B and D. The sensor control circuit 30 is so designed that the voltages developed at the terminals B and D during the determination of the impedance Zac may lie within the operational voltage range (0 to 5V) of the A/D converters A/D2 and A/D3.

The sensor control circuit 30 of the second embodiment may be modified as illustrated in FIG. 5 or 6.

Specifically, the sensor control circuit 30 may be designed to have structure of FIG. 5 to amplify a potential difference between the reference voltage Vf and the voltage at the terminal B through the operational amplifier 41. Alternatively, the sensor control circuit 30 may be designed to have the switch 39 and the capacitor 40, as used in the structure of FIG. 6, installed in a line extending from the terminal B of the current-measuring resistor 32 to a junction of the operational amplifier 41 and a wide range A/F measuring output port leading to the A/D converter A/D0 of the microcomputer 20 to avoid output of an undesirable change in current flowing through the current-measuring resistor 32 during measurement of the impedance Zac.

Figure 8:
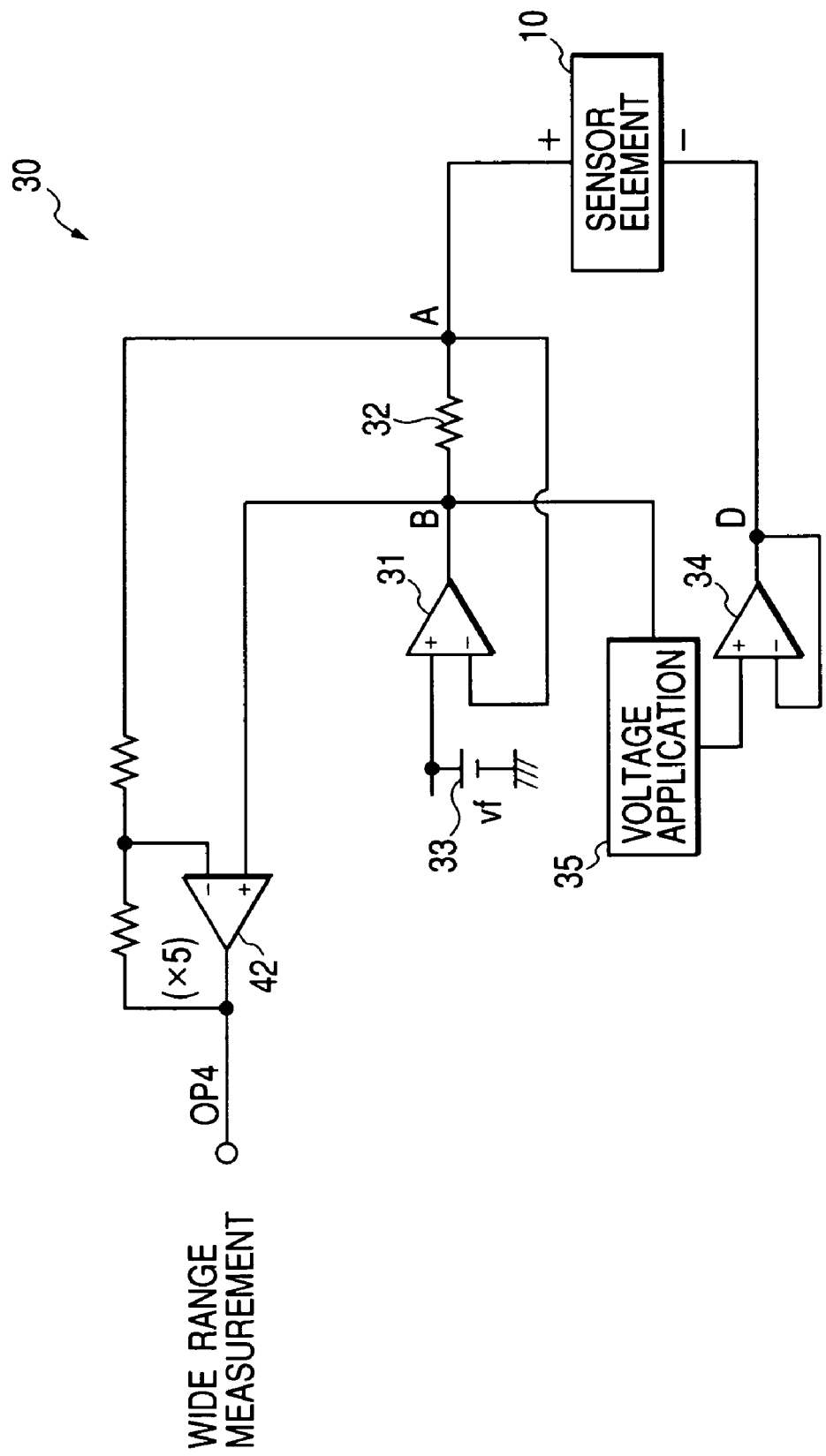
FIG. 8 is a circuit diagram which shows an electric structure of a sensor control circuit of a gas concentration measuring apparatus according to the third embodiment of the invention.

FIG. 8 shows the sensor control circuit 30 according to the third embodiment of the invention which is different from the first embodiment in that the wide range measuring signal is outputted through one channel equipped with an operational amplifier 42 whose amplification factor is five (5).

The resolution of the sensor control circuit 30 in determining the A/F ratio will be evaluated below.

The A/F measuring range of the sensor control circuit 30 of this embodiment is, like the first embodiment, between an A/F ratio of 11 and the free-air ratio. Other electrical specifications of the sensor element 10 and the sensor control circuit 30 are the same as those in the first embodiment.

The wide range measuring signal or an output OP4 of the operational amplifier 42 has values, as shown below, at the free-air ratio and an A/F ratio of 11, respectively.

$OP4=2.5V+185\Omega \times 2.5$ mA$\times 5=4.8125V$ $OP4=2.5V+185\Omega \times (-1.35$ mA$)\times 5=1.2975V$ In a case where the A/D converter A/D0 is implemented by a 10-bit A/D converter, the A/F ratio measurement resolution within the range of an A/F of 11 to the free-air ratio is expressed below on the numerical conditions as described in the first embodiment.

$(4.8125-1.2975)/5V\times 1024=720$

It is found that the A/F ratio measurement resolution is five times (720/144=5) greater than that in the conventional structure, as illustrated in FIG. 16.

If a current change corresponding to an A/F ratio of one (1) in the vicinity of the stoichiometric air-fuel ratio is 0.22 mA, the A/F ratio measurement resolution is $0.2$ mA$\times 185\Omega \times 5/5V\times 1024=37$ In this case, the resolution will be 0.03A/F per LSB which is somewhat lower than that in the above embodiment in the vicinity of the stoichiometric air-fuel ratio, but higher than that in the conventional structure of FIG. 16.

The sensor element impedance Zac is, like the first embodiment, determined using changes in voltage at the terminals B and D. The sensor control circuit 30 is so designed that the voltages developed at the terminals B and D during the determination of the impedance Zac may lie within the operational voltage range (0 to 5V) of the A/D converters A/D2 and A/D3.

The sensor control circuit 30 of the third embodiment may be modified as illustrated in FIG. 5 or 6.

Specifically, the sensor control circuit 30 may be designed to have structure of FIG. 5 to amplify a potential difference between the reference voltage Vf and the voltage at the terminal B through the operational amplifier 42. Alternatively, the sensor control circuit 30 may be designed to have the switch 39 and the capacitor 40, as used in the structure of FIG. 6, installed in a line extending from the terminal B of the current-measuring resistor 32 to the operational amplifier 42 to avoid output of an undesirable change in current flowing through the current-measuring resistor 32 during measurement of the impedance Zac.

Figure 9:
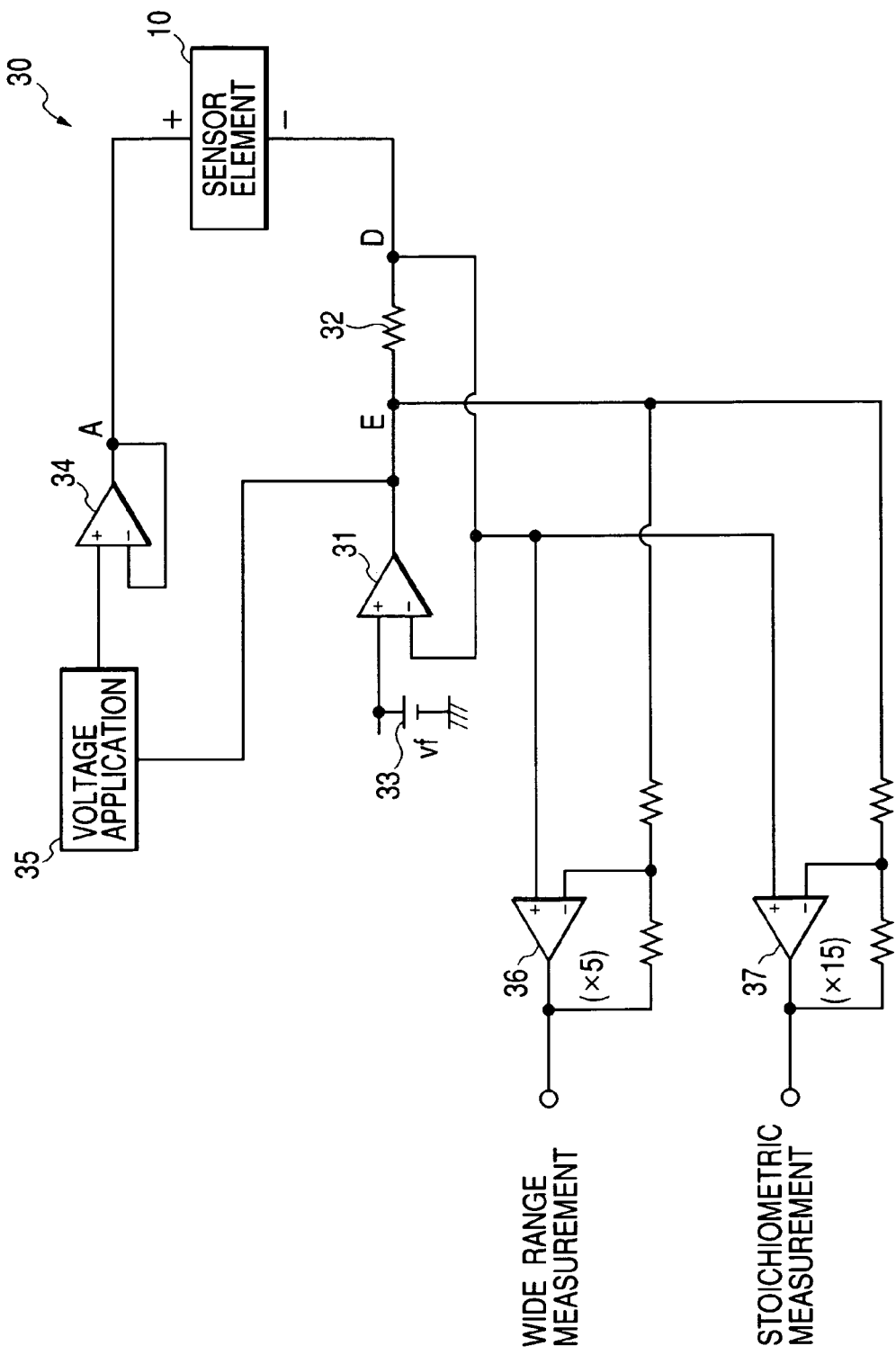
FIG. 9 is a circuit diagram which shows an electric structure of a sensor control circuit of a gas concentration measuring apparatus according to the fourth embodiment of the invention.

FIG. 9 shows the sensor control circuit 30 according to the fourth embodiment of the invention. In each of the first to third embodiments, the current-measuring resistor 32 is connected to the positive terminal of the sensor element 10. The voltage application control circuit 35 is connected to the negative terminal of the sensor element 10. The structure of this embodiment is so designed that the current-measuring resistor 32 is connected to the negative terminal of the sensor element 10m and the voltage application control circuit 35 is connected to the positive terminal of the sensor element 10. The same reference numbers as those in the above embodiments refer to the same parts, and explanation thereof in detail will be omitted here. The structure of this embodiment may also be used with each of the second and third embodiments as illustrated in FIGS. 7 and 8.

The voltage used to measure the A/F ratio and the ac voltage change used to measure the impedance Zac are applied to the positive terminal of the sensor element 10 through the operational amplifier 34. When the exhaust gasses are lean, the current flows through the current-measuring resistor 32 in a direction from the terminal D to the terminal E, thereby causing the voltage at the terminal E to drop below that at the terminal D. Alternatively, when the exhaust gasses are rich, the current flows through the current-measuring resistor 32 in a direction from the terminal E to the terminal D, thereby causing the voltage at the terminal E to rise above that at the terminal D. This causes a potential depending upon the A/F ratio to be reversed in level, so that feedback currents of the operational amplifiers 36 and 37 flow to the terminal E. The feedback currents are absorbed by the operational amplifier 31, thus eliminating the effects thereof on the current flowing through the current-measuring resistor 32. This eliminates the need for an additional operational amplifier such as the operational amplifier 38, as illustrated in FIGS. 5 and 6, used to absorb the feedback currents, thus resulting in a simplified structure.

The sensor control circuit 30 of this embodiment may be designed to have the switch 39 and the capacitor 40, as used in the structure of FIG. 6, installed in a line extending from the terminal E to the operational amplifiers 36 and 37 to avoid output of an undesirable change in current flowing through the current-measuring resistor 32 during measurement of the impedance Zac.

Figure 10:
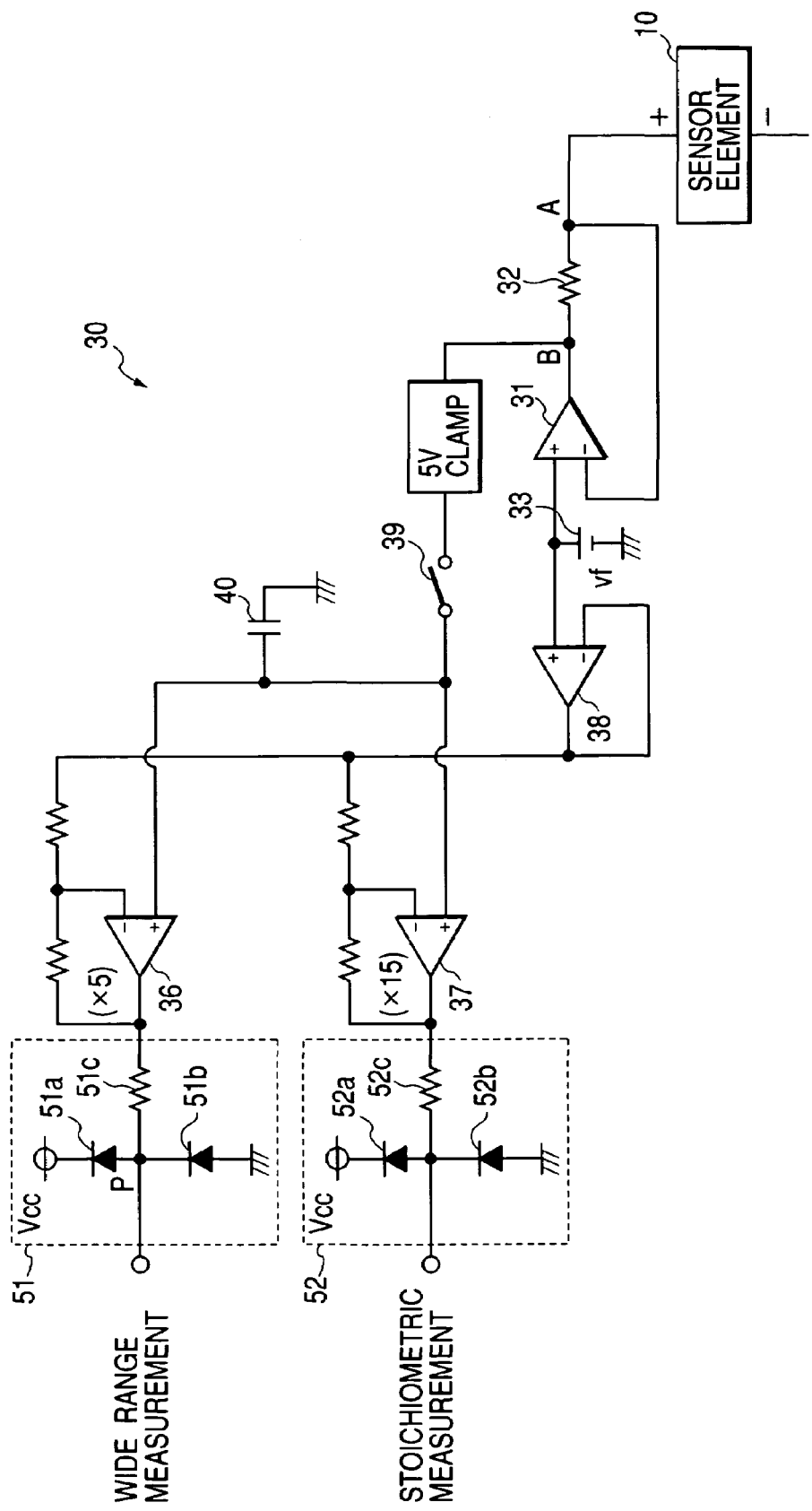
FIG. 10 is a circuit diagram which shows a third modification of a sensor control circuit.

The sensor control circuit 30 may also be modified as discussed below. In each of the structures as shown in FIGS. 1 and 7, a voltage exceeding 5V that is out of the operating voltage of the A/D converter A/D1 may be outputted through the operational amplifier 37 or 41 whose amplification factor is 15, which results in latch-up of the A/D converter. In order to protect the A/D converter, it is advisable that the output of the operational amplifier 37 or 41 be limited to near a maximum operating voltage of the A/D converter. Such limitation may be achieved by use of 5V-clamping circuits as discussed below with reference to FIG. 10.

Specifically, the clamping circuits 51 and 52 are installed in connection with the outputs of the operational amplifiers 36 and 37. The clamping circuit 51 is made up of diodes 51a and 51b and a resistor 51c. Similarly, the clamping circuit 52 is made up of diodes 52a and 52b and a resistor 52c. The diode 51a of the clamping circuit 51 is connected to a terminal P of an output line of the operational amplifier 36 leading to an output port for the wide range measuring signal and oriented in a forward direction to a constant voltage source Vcc (5V=a maximum operating voltage of the A/D converters A/D0 and A/D1 of the microcomputer 20). If a voltage drop of the diode 51a is 0.7V, the voltage appearing at the terminal P is kept at a maximum level of 5V+0.7V. The clamping circuit 52 is identical in structure with the clamping circuit 51, and explanation thereof in detail will be omitted here. Therefore, outputs of the operational amplifiers 36 and 37 are restricted to near the maximum operating voltage of the A/D converters A/D0 and A/D1 of the microcomputer 20.

Figure 11:
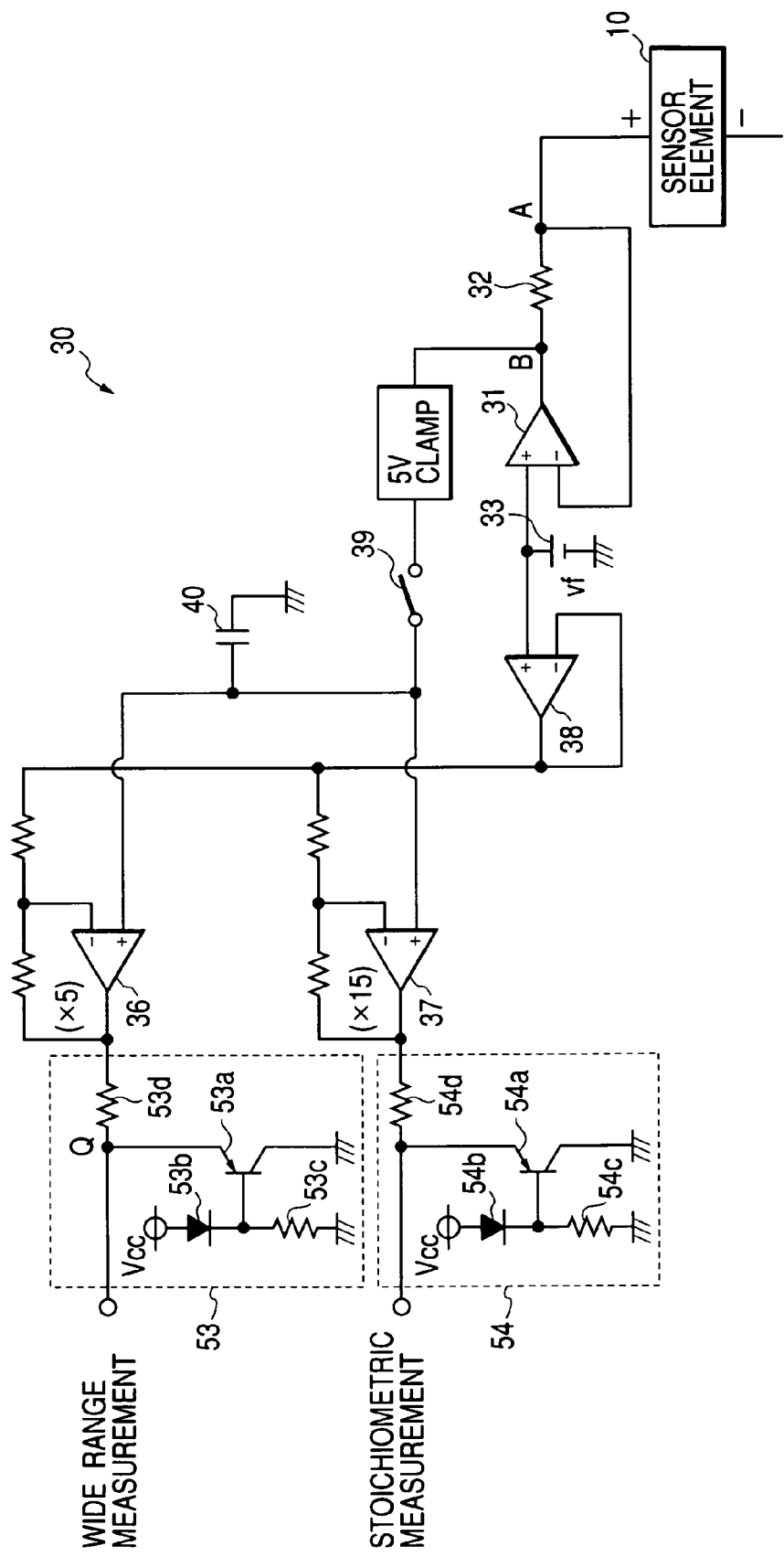
FIG. 11 is a circuit diagram which shows a fourth modification of a sensor control circuit.

Instead of the clamping circuits 51 and 52, clamping circuits 53 and 54, as shown in FIG. 11, may be employed. The clamping circuit 53 is made up of a pnp transistor 53a, a diode 53b, and resistors 53c and 53d. Similarly, the clamping circuit 54 is made up of a pnp transistor 54a, a diode 54b, and resistors 54c and 54d. The transistor 53a of the clamping circuit 53 is connected at an emitter thereof to a terminal Q of an output line of the operational amplifier 36 leading to an output port for the wide range measuring signal and at a base thereof to a reference voltage supply circuit made up of a constant voltage source Vcc (5V), the diode 53b, and the resistor 53c. The diode 53c is connected to the constant voltage source Vcc in the reverse direction thereto. If a voltage drop of the diode 53b is 0.7V, the voltage inputted to the base of the transistor 53a is kept at 4.3V. If an emitter-to-base voltage drop of the transistor 53a is 0.7V, the terminal Q is kept at approximately 5V. The clamping circuit 54 is identical in structure with the clamping circuit 53, and explanation thereof in detail will be omitted here. Outputs of the operational amplifiers 36 and 37 are, therefore, restricted to near the maximum operating voltage of the A/D converters A/D0 and A/D1 of the microcomputer 20.

The sensor control circuit 30 of each of the first, second, and fourth embodiments is designed to have two A/F ratio measuring ranges: the wide A/F ratio measuring range of an A/F ratio of 11 to the free-air ratio and the narrow A/F ratio measuring range of an A/F ratio of 12 to 22, but however, may be designed to have three or more A/F ratio measuring ranges. The wide A/F ratio measuring range and the narrow A/F ratio measuring range may alternatively be defined by values other than the above specified A/F ratios. For instance, one of the two ranges may be defined between A/F ratios of 11 and 22, and the other may be defined between an A/F ratio of 11 and the free-air ratio. Additionally, the two ranges may overlap partially with each other or be separate from each other.

Specifically, the sensor control circuit 30 may have a first amplifier which has an amplification factor of m and works to produce a first A/F ratio measuring signal used to determine the A/F ratio within a first A/F ratio measuring range and a second amplifier which has an amplification factor of n (>m) and works to produce a second A/F ratio measuring signal used to determine the A/F ratio within a second A/F ratio measuring range different from the first A/F ratio measuring range.

The sensor control circuit 30 of each embodiment works to determine the sensor element impedance Zac as a function of a change in current produced by the sensor element 10 as measured by the resistor 32, but may be designed to measure the current change or a change in voltage produced by the sensor element 10 without use of the resistor 32 or alternatively be designed not to measure the sensor element impedance Zac.

Figure 12:
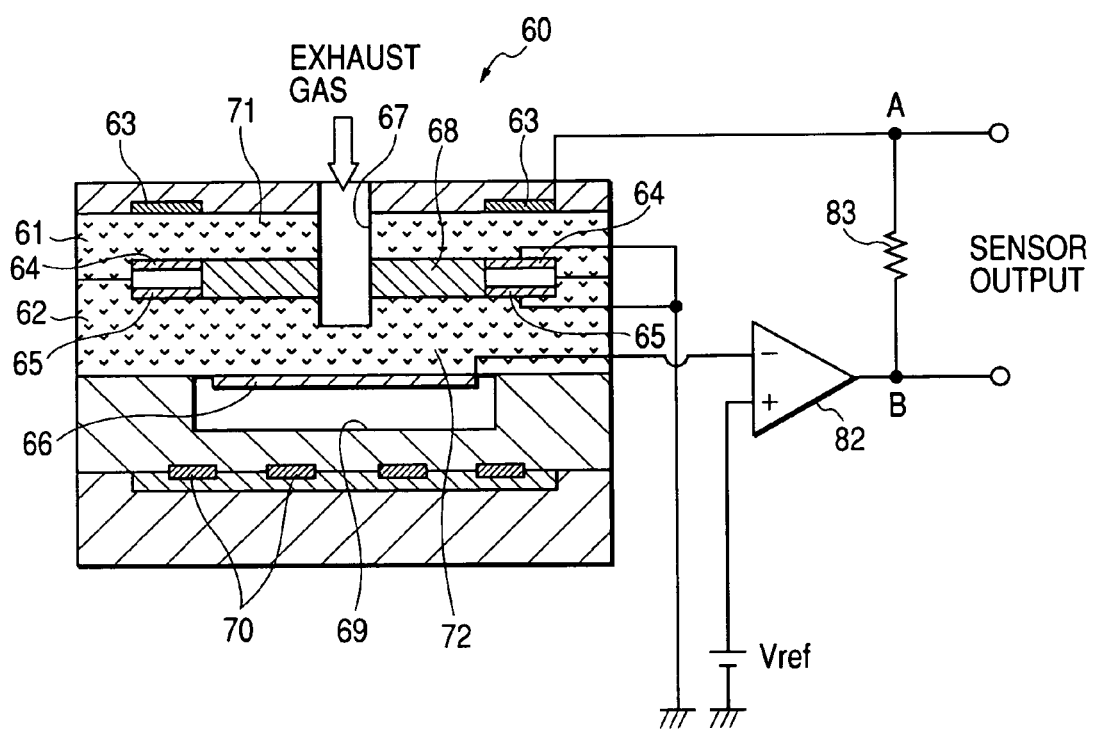
FIG. 12 is a transverse sectional view which shows a first modification of a sensor element.

The sensor control circuit 30 may also be used with a sensor element different in type from the one shown in FIG. 2. For instance, a sensor element 60, as illustrated in FIG. 12, may be employed. The sensor element 60 includes two solid electrolyte layers 61 and 62. The solid electrolyte layer 61 has electrodes 63 and 64 affixed to opposed surfaces thereof. Similarly, the solid electrolyte layer 62 has electrodes 65 and 66 affixed to opposed surfaces thereof. Each of the electrodes 63, 64, and 65 is viewed in the drawing as being made up of right and left separate parts, but, it is, in practice, formed by a single plate having a connecting portion (not shown) extending in a transverse direction in the drawing.

The solid electrolyte layer 61 and the electrodes 63 and 64 constitute the so-called pump cell. The solid electrolyte layer 62 and the electrodes 65 and 66 constitute an oxygen sensor cell 72. The sensor element 60 also includes a gas inlet 67 through which exhaust gasses of the automotive engine enter and a porous diffusion layer 68, an air duct 69, and a heater 70. The structure and operation of this type of sensor element are disclosed in, for example, U.S. Pat. No. 6,295,862 B1, assigned to the same assignee as that of this application, disclosure of which is incorporated herein by reference.

The potential at the electrode 66 of the oxygen sensor cell 72 is inputted to the negative (−) input terminal of a comparator 82. To the positive (+) input terminal of the comparator 82, a reference voltage Vref is inputted. A current-measuring resistor 83 is disposed between the electrode 63 of the pump cell 71 and an output terminal of the comparator 82. The sensor element 60 outputs electric signals as sensor outputs from terminals A and B leading to ends of the resistor 83.

The oxygen sensor cell 72 works to produce an electromotive force which has one of two discrete values (e.g., 0V and 0.9V) selectively as a function of whether the exhaust gasses are on the rich side or the lean side of the stoichiometric air-fuel ratio. When the exhaust gasses are on the lean side, the oxygen sensor cell 72 produces a lower electromotive force, so that an output of the comparator 82 (i.e., the voltage appearing at the terminal B) rises in level. This causes the current to flow through the current-measuring resistor 83 in a direction from the terminal B to the terminal A. Conversely, when the exhaust gasses are on the rich side, the oxygen sensor cell 72 produces a higher electromotive force, so that an output of the comparator 82 (i.e., the voltage appearing at the terminal B) drops in level. This causes the current to flow through the current-measuring resistor 83 in a direction from the terminal A to the terminal B. Note that the oxygen sensor cell 72 is also called as an electromotive force cell or an oxygen concentration measuring cell.

Figure 13:
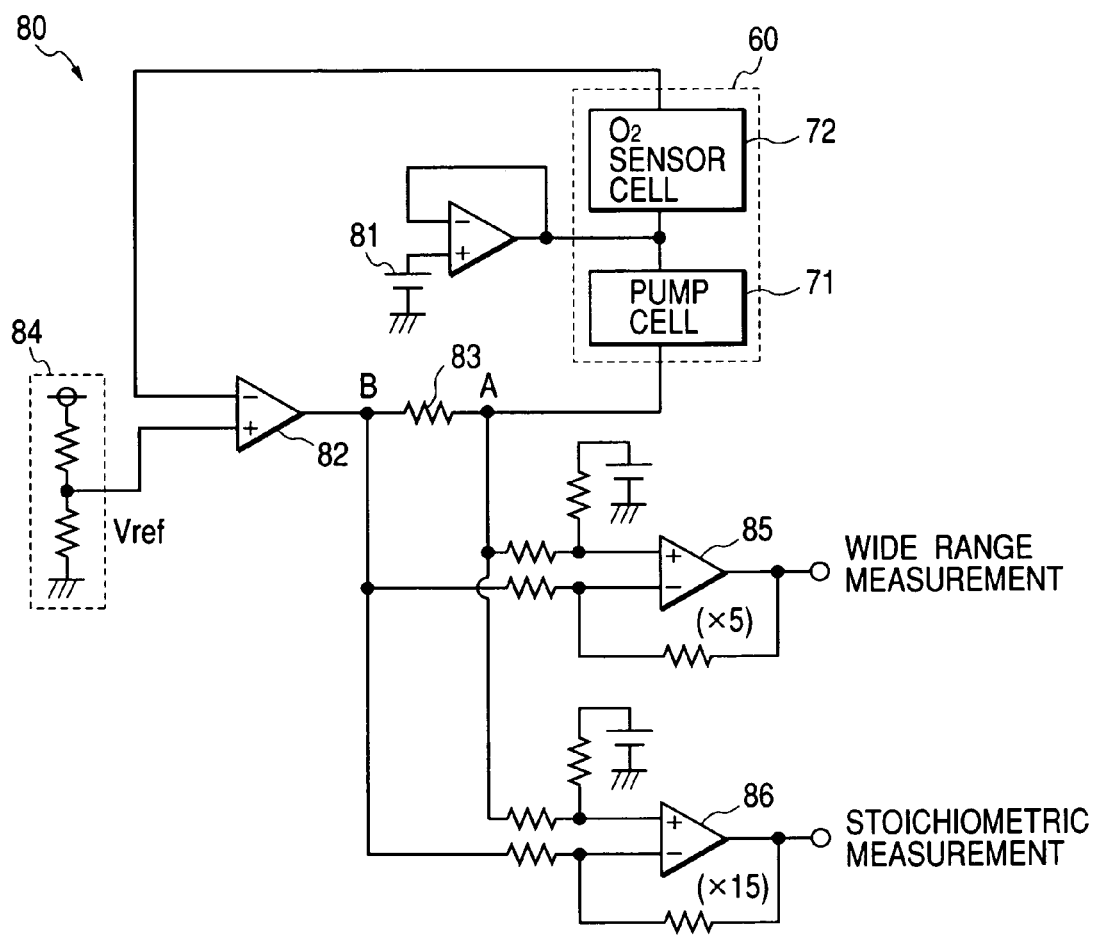
FIG. 13 is a circuit diagram which shows a sensor control circuit used with the sensor element as illustrated in FIG. 12.

FIG. 13 shows a sensor control circuit 80 used with an A/F sensor equipped with the sensor element 60, as illustrated in FIG. 12.

The sensor control circuit 80 includes a reference voltage source 81, operational amplifiers 82, 85, and 86, and a reference voltage generating circuit 84. The reference voltage source 81 is connected to a common junction of the oxygen sensor cell 72 and the pump cell 71. The oxygen sensor cell 72 and the pump cell 71 form a closed loop together with the operational amplifier 82 and the resistor 83. The reference voltage generating circuit 84 works to apply a reference voltage Vref (e.g., 0.45V) to a non-inverting input (+) of the operational amplifier 82. When the exhaust gases are lean, the current flows, as described above, through the current-measuring resistor 83 in the direction from the terminal B to the terminal A. Conversely, when the exhaust gasses are rich, the current flows through the current-measuring resistor 83 in the direction from the terminal A to the terminal B. The sensor control circuit 80 also includes a feedback circuit (not shown) which works to control the voltage applied to the pump cell 71 to bring an output voltage of the oxygen sensor cell 72 into agreement with a target one. This feedback control is known in the art, and explanation thereof in detail will be omitted here.

The operational amplifier 85 has an amplification factor of 5 and is connected to the terminals A and B of the resistor 83. The operational amplifier 85 works to produce the wide range A/F ratio measuring signal used to determine the A/F ratio within the wide A/F ratio measuring range of, for example, an A/F ratio of 11 to the free-air ratio (i.e., an overall range of the A/F ratios). The operational amplifier 86 has an amplification factor of 15 and is connected to the terminals A and B of the resistor 83. The operational amplifier 86 works to produce the stoichiometric air-fuel ratio measuring signal used to determine the A/F ratio within the narrow A/F ratio measuring range of, for example, A/F ratios of 12 to 22 containing the stoichiometric air-fuel ratio.

The sensor control circuit 80 provides the same effects as described in the first embodiment that the A/F ratio measurement resolution is improved over the overall range of the A/F ratios.

Figure 14:
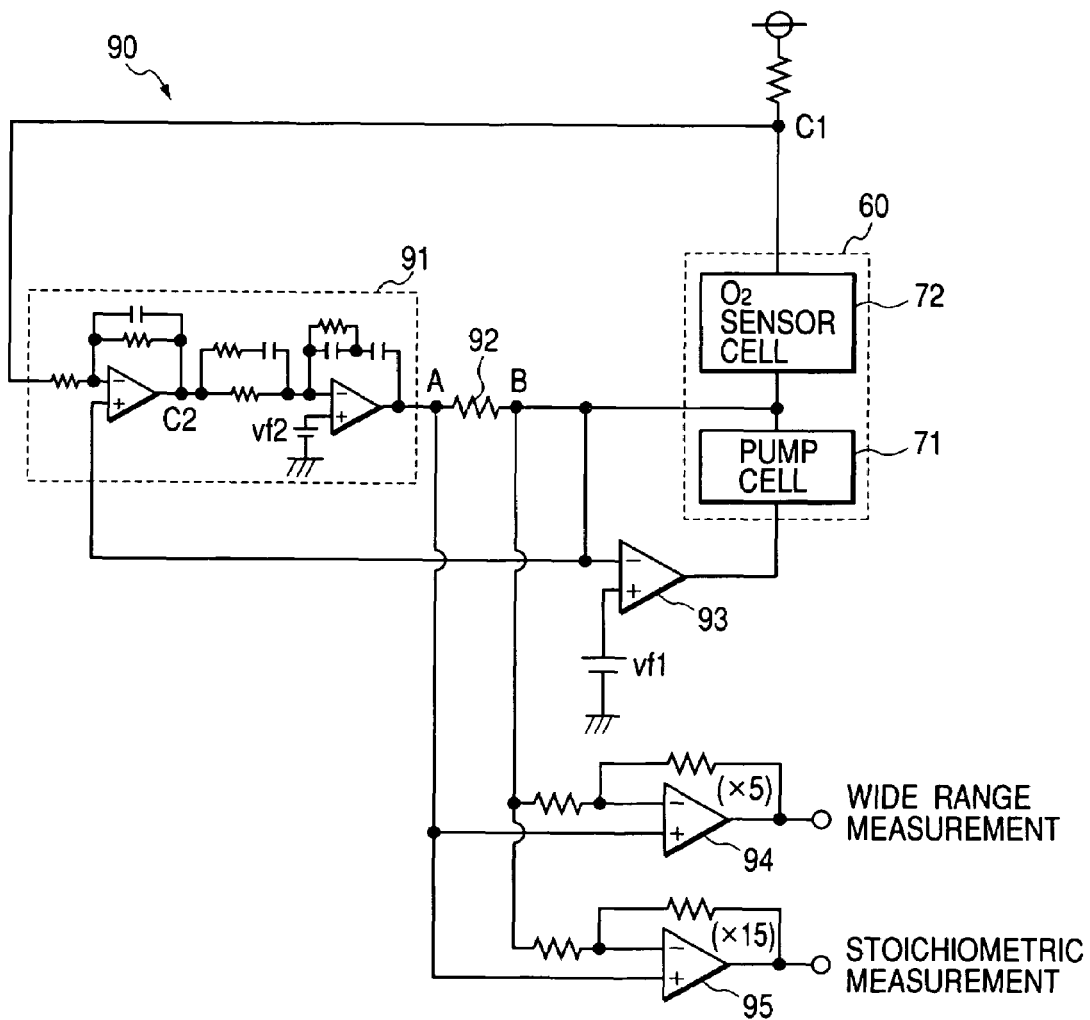
FIG. 14 is a circuit diagram which shows a modification of sensor control circuit which may be employed with the sensor element as illustrated in FIG. 12.

In the sensor control circuit 80, the voltages appearing at the terminals A and B both vary. A structure designed to hold the voltage developed at one of the terminals A and B at a constant value is shown in FIG. 14.

The sensor control circuit 90 works to apply the voltage identical with the reference voltage V$f1$ (e.g., 3V) to the common terminal of the pump cell 71 and the oxygen sensor cell 72 through the operational amplifier 93. The voltage developed at the terminal B is, therefore, kept at 3V. The sensor control circuit 90 also includes a closed loop made up of the oxygen sensor cell 72, a feedback circuit 91, and a current-measuring resistor 92. The feedback circuit 91 is designed to produce a reference voltage V$f2$ of, for example, 2.55V.

The operation of the sensor control circuit 90 in an example where the exhaust gasses are rich will be described below.

When the exhaust gasses are rich, the oxygen sensor cell 72 produces an electromotive force to elevate the voltage at the terminal C1 up to 3.45V, so that the potential at the terminal C2 of the feedback circuit 91 drops. This causes the output of the feedback circuit 91, that is, the voltage at the terminal A to rise. The current, thus, flows through the current-measuring resistor 83 in a direction from the terminal A to the terminal B. Conversely, when the exhaust gasses are lean, the current flows through the current-measuring resistor 83 in a direction from the terminal B to the terminal A.

The sensor control circuit 90 also includes operational amplifiers 94 and 95 which are connected to the terminals A and B of the current-measuring resistor 92. The operational amplifier 94 has an amplification factor of 5 and works to produce the wide range A/F ratio measuring signal used to determine the A/F ratio within the wide A/F ratio measuring range of, for example, an A/F ratio of 11 to the free-air ratio (i.e., an overall range of the A/F ratios). The operational amplifier 95 has an amplification factor of 15 and works to produce the stoichiometric air-fuel ratio measuring signal used to determine the A/F ratio within the narrow A/F ratio measuring range of, for example, A/F ratios of 12 to 22 containing the stoichiometric air-fuel ratio.

The sensor control circuit 90 provides the same effects as described in the first embodiment that the A/F ratio measurement resolution is improved over the overall range of the A/F ratios.

Figure 15:
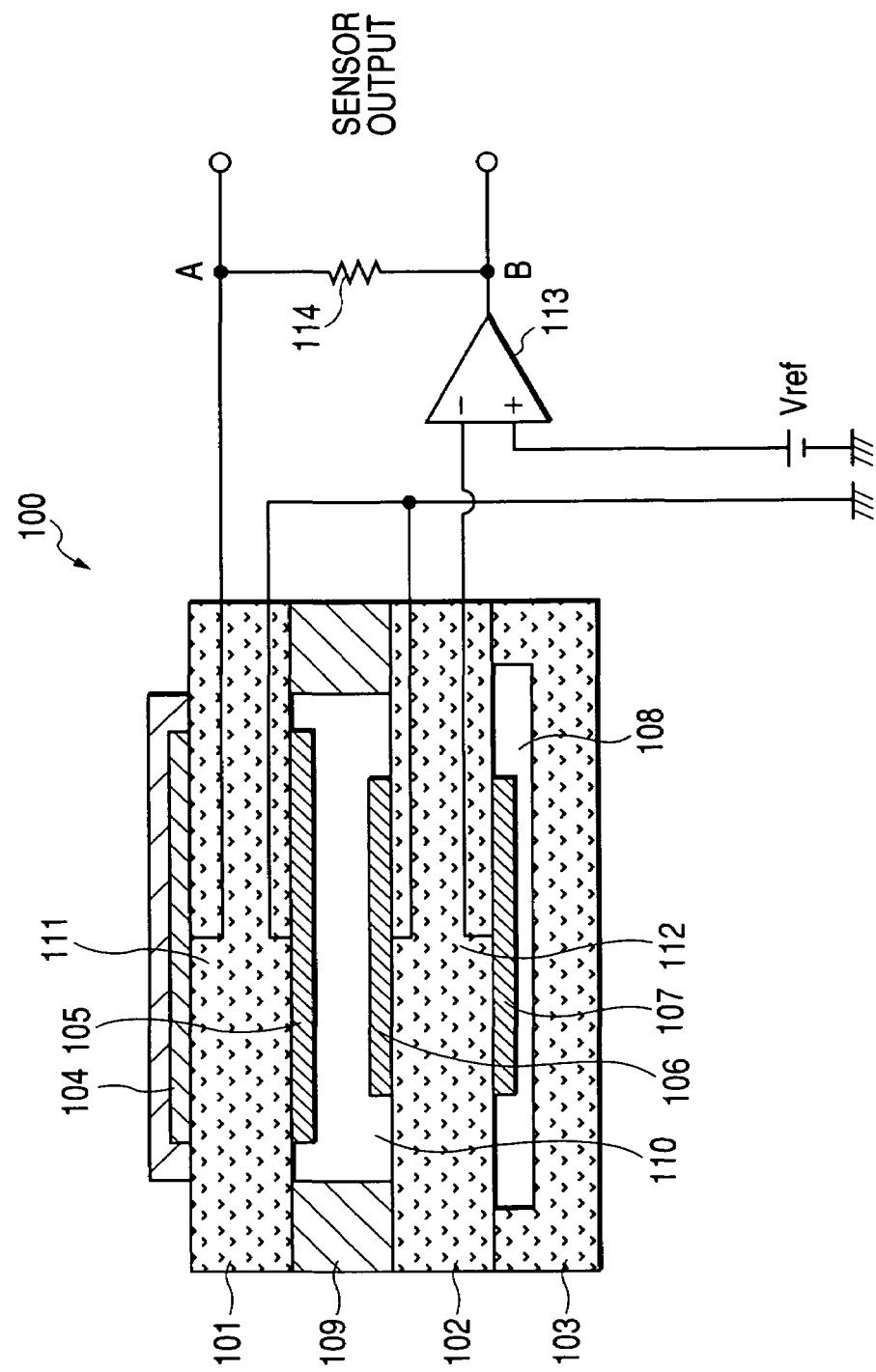
FIG. 15 is a transverse sectional view which shows a second first modification of a sensor element.

FIG. 15 shows a sensor element 100 which may be employed in the gas concentration measuring apparatus of each of the above embodiments.

The sensor element 100 includes three solid electrolyte layers 101, 102, and 103. The solid electrolyte layer 101 has electrodes 104 and 105 affixed to opposed surfaces thereof. Similarly, the solid electrolyte layer 102 has electrodes 106 and 107 affixed to opposed surfaces thereof. The solid electrolyte layer 101 and the electrodes 104 and 105 form a pump cell 111. The solid electrolyte layer 102 and the electrodes 106 and 107 form an oxygen sensor cell 112. The solid electrolyte layer 103 forms a wall defining an oxygen reference chamber 108. The sensor element 60 is, like the above embodiment, of a laminated structure. The sensor element 100 also includes a porous diffusion layer 109 and a gas chamber 110 into which exhaust gasses of the automotive engine enter. The oxygen sensor cell 112 operates like the oxygen sensor cell 72 as illustrated in FIG. 12.

The potential at the electrode 107 of the oxygen sensor cell 112 is inputted to the negative (−) input terminal of a comparator 113. To the positive (+) input terminal of the comparator 113, a reference voltage Vref is inputted. A current-measuring resistor 114 is disposed between the electrode 104 of the pump cell 111 and an output terminal of the comparator 113. The sensor element 100 outputs electric signals as sensor outputs from terminals A and B leading to ends of the resistor 114.

The two-cell sensor elements 60 and 100, as illustrated in FIGS. 12 and 15, are designed to control the voltage applied to the oxygen sensor cells 72 and 112 to measure an internal resistance of the oxygen sensor cells 71 and 112 in a cycle. Taking as an example the sensor element 100, when an internal resistance measuring cycle is entered, the oxygen sensor cell 112 is so controlled as to produce a flow of a predetermined current, which results in a change in voltage at the oxygen sensor cell 112 as a function of the internal resistance thereof. The sensor control circuit 30 monitors such a voltage change to determine the internal resistance of the oxygen sensor cell 112. More specifically, the sensor control circuit 30 works to control the oxygen sensor cell 112 to produce a flow of a constant current reverse in polarity to an electromotive force occurring in the oxygen sensor cell 112 for a given period of time and measure a change in voltage developed across the oxygen sensor cell 112. The sensor control circuit 30 may also work to measure a change in voltage across the pump cell 111 in a similar manner to determine an internal resistance of the pump cell 111. After completion of measurement of the internal resistance, the sensor control circuit 30 may create a flow of a current reverse in polarity to the current produced to measure the internal resistance for a given period of time for returning the sensor element 100 back to a condition quickly which permits the concentration of oxygen ($O_2$) to be measured.

For instance, the measurement of the internal resistance of the oxygen sensor cell 112 may be achieved by applying an ac pulse signal having a constant frequency (e.g., several kHz) to the oxygen sensor cell 112 and monitoring a change in voltage developed across the oxygen sensor cell 112 which is a function of the internal resistance of the oxygen sensor cell 112.

The gas concentration measuring apparatus, as described in each of the above embodiments, may be used with a composite gas concentration measuring sensor which includes first and second cells made of a solid electrolyte body. The first cell works as a pump cell to pump oxygen molecules out of or into a first gas chamber formed in a sensor body and output a signal indicative of the concentration of the pumped oxygen molecules. The second cell works as a sensor cell to produce a signal indicative of the concentration of a preselected component of gasses flowing into a second gas chamber from the first gas chamber. For example, the composite gas concentration measuring sensor may be used to measure the concentration NOx contained in exhaust gasses of the automotive engine. Further, the composite gas concentration measuring sensor may be designed to have a third cell serving as a monitor cell or a second pump cell to measure the concentration of oxygen molecules remaining in the second gas chamber.

The gas concentration measuring sensor may alternatively be designed to measure the concentration of HC or CO contained in the exhaust gasses of the automotive engine. The measurement of concentration of HC or CO is achieved by pumping excessive oxygen ($O_2$) out of the first gas chamber using the pump cell and decomposing HC or CO contained in the gasses entering the second gas chamber using the sensor cell to produce an electric signal indicative of the concentration of HC or CO.

The gas concentration measuring apparatus in each of the above embodiment may alternatively be employed to measure the concentration of a gas other than a preselected component contained in exhaust emissions of automotive engines.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A gas concentration measuring apparatus comprising:
a gas concentration sensor equipped with a sensor element formed by a lamination of a solid electrolyte plate, a diffusion layer, and an insulating layer and working to produce an electric signal as a function of a concentration of a preselected component of gasses over a given wide gas concentration measuring range;
a sensor circuit including a current-measuring resistor, a plurality of amplifiers, and A/D converters, said sensor circuit working to apply a voltage to the sensor element, the current-measuring resistor functioning to measure a current signal flowing through the sensor element produced upon application of the voltage to the sensor element, the amplifiers having predetermined amplification factors different from each other and each working to amplify the current signal as measured by the current-measuring resistor to output the amplified current signal to the A/D converters to determine the concentration of the preselected component of the gasses within a corresponding one of a plurality of measurement ranges defined within the given wide gas concentration measuring range, respectively;
clamping circuits disposed in output lines leading to output terminals of the amplifiers, respectively, each of the clamping circuits working to hold the amplified current signal outputted from a corresponding one of the amplifiers within an operating voltage range of a corresponding one of the A/D converters; and a resistance measuring circuit working to change one of a voltage and a current applied to the sensor element in an ac form and measure one of a resultant change in voltage and a resultant change in current, as sampled through the current-measuring resistor, to determine a resistance of the sensor element in order to control a degree of activation of the sensor element;

wherein each of the clamping circuits includes a pnp transistor and a constant voltage source, the pnp transistor being connected at an emitter thereof to the output lines of a corresponding one of the amplifiers and at a base thereof to a reference voltage source, the constant voltage source generating a constant voltage substantially identical with a maximum operating voltage of a corresponding one of the A/D converters, and wherein each of the clamping circuits is so designed that an input voltage appearing at the base of the pnp transistor is identical with a value derived by subtracting a base-emitter voltage drop of the pnp transistor from the constant voltage generated by the constant voltage source.

2. A gas concentration measuring apparatus as set forth in claim 1, wherein the plurality of measurement ranges include a first measurement range and a second measurement range narrower than the first measurement range, and wherein the plurality of amplifiers include a first amplifier which has an amplification factor m and serves to produce a wide range output used to determine the concentration of the preselected component within the first measurement range and a second amplifier which has an amplification factor n and serves to produce a narrow range output used to determine the concentration of the preselected component within the second measurement range, the amplification factor m being smaller than the amplification factor n.

3. A gas concentration measuring apparatus as set forth in claim 1, wherein the plurality of measurement ranges include an overall measurable range occupying the whole of the given wide gas concentration measuring range and a partial measurable range occupying a portion of the overall measurable range, and wherein the plurality of amplifiers include a first amplifier which has an amplification factor m and serves to produce a wide range output used to determine the concentration of the preselected component within the overall measurable range and a second amplifier which has an amplification factor n and serves to produce a narrow range output used to determine the concentration of the preselected component within the partial measurable range, the amplification factor m being smaller than the amplification factor n.

4. A gas concentration measuring apparatus as set forth in claim 3, wherein the sensor element is so designed as to measure an air-fuel ratio of a burned gas over the given wide gas concentration measuring range, and wherein the partial measurable range including a stoichiometric air-fuel ratio.

5. A gas concentration measuring apparatus as set forth in claim 1, further comprising a resistance measuring circuit working to change one of a voltage and a current applied to the sensor element in an ac form and measure one of a resultant change in voltage and a resultant change in current through the current-measuring resistor to determine a resistance of the sensor element.

6. A gas concentration measuring apparatus as set forth in claim 1, wherein the sensor element is so designed that the change in current to determine the resistance of the sensor element is greater than said current signal.

7. A gas concentration measuring apparatus as set forth in claim 1, wherein the sensor element is so designed as to measure an air-fuel ratio of a burned gas over the given wide gas concentration measuring range.

8. A gas concentration measuring apparatus as set forth in claim 1, wherein the sensor element is formed by a lamination of a pump cell working to pump oxygen into or out of a gas chamber defined in the sensor element filled with the gasses and an oxygen sensor cell working to output a signal as a function of concentration of oxygen contained in the gasses, and wherein said sensor circuit controls the pump cell so as to keep the signal outputted by the oxygen sensor cell at a given value.

9. A gas concentration measuring apparatus as set forth in claim 8, wherein said sensor circuit works to produce a voltage as a function of an internal resistance of the sensor element.

10. A gas concentration measuring apparatus as set forth in claim 9, wherein said gas concentration sensor is implemented by an air-fuel ratio sensor designed to measure an air-fuel ratio of a burned gas over the given wide gas concentration measuring range.

11. A gas concentration measuring apparatus as set forth in claim 1, wherein the sensor element includes a plurality of cells made of a solid electrolyte material, one of which forms a first cell working to pump oxygen into or out of a gas chamber defined in the sensor element filled with the gasses, and another of which forms a second cell working to output a signal as a function of concentration of the preselected component of the gasses into or form which the oxygen is pumped by the first cell.

12. A gas concentration measuring apparatus as set forth in claim 1, wherein each of the amplifiers is connected to the current-measuring resistor so that voltage developed across ends of the current-measuring resistor is applied across a positive and a negative terminal of the operational amplifier, and wherein said sensor circuit includes a feedback current path for each of the amplifiers and an operational amplifier installed in each of the feedback current paths to absorb a feedback current of a corresponding one of the amplifiers.

13. A gas concentration measuring apparatus as set forth in claim 1, wherein the current-measuring resistor has a first and a second terminal, wherein said sensor circuit works to apply a fixed reference voltage to the first terminal of the current-measuring resistor, change one of a voltage and a current applied to the sensor element in an ac form, and measure a resultant voltage developed at the second terminal to determine a resistance of the sensor element, and wherein said sensor circuit has a switch working to open and close between the second terminal and the amplifiers.

14. A gas concentration measuring apparatus as set forth in claim 13, wherein said sensor circuit has a capacitor installed between the switch and the amplifiers to hold a voltage developed immediately before the switch is opened.

* * * * *